United States Patent
Futamura

(10) Patent No.: US 9,445,942 B2
(45) Date of Patent: Sep. 20, 2016

(54) HOLDING DEVICE FOR CONTACT LENS FOR VITREOUS SURGERY, HOLDING DEVICE SET, AND CONTACT LENS FOR VITREOUS SURGERY, AND LENS SET

(75) Inventor: Hideyuki Futamura, Saitama (JP)

(73) Assignee: Hoya Corporation, Tokyo (JP)

( * ) Notice: Subject to any disclaimer, the term of this patent is extended or adjusted under 35 U.S.C. 154(b) by 1087 days.

(21) Appl. No.: 13/390,512

(22) PCT Filed: Aug. 16, 2010

(86) PCT No.: PCT/JP2010/063815
§ 371 (c)(1),
(2), (4) Date: Feb. 24, 2012

(87) PCT Pub. No.: WO2011/021601
PCT Pub. Date: Feb. 24, 2011

(65) Prior Publication Data
US 2012/0140180 A1    Jun. 7, 2012

(30) Foreign Application Priority Data

Aug. 18, 2009 (JP) .................. 2009-189055
Nov. 13, 2009 (JP) .................. 2009-260082

(51) Int. Cl.
| A61F 9/007 | (2006.01) |
| A61F 9/009 | (2006.01) |
| A61F 9/008 | (2006.01) |

(52) U.S. Cl.
CPC .......... *A61F 9/00736* (2013.01); *A61F 9/009* (2013.01); *A61F 2009/00874* (2013.01); *A61F 2009/00887* (2013.01)

(58) Field of Classification Search
CPC .... A61F 9/00736; A61F 9/009; A61F 9/013; A61F 9/0008; A61F 9/0061; A61F 9/0026; A61F 9/0017; A61F 2009/00874; A61F 2009/00887; A61F 2009/00889; A61F 2009/0052; A61F 2009/0043; A61F 2009/0035; A61F 2009/0026
See application file for complete search history.

(56) References Cited

U.S. PATENT DOCUMENTS

| 6,412,946 B1 | 7/2002 | Vijfvinkel |
| 2003/0014106 A1 | 1/2003 | Kita |

(Continued)

FOREIGN PATENT DOCUMENTS

| EP | 1295579 A1 | 3/2003 |
| JP | 2003-24366 A | 1/2003 |

(Continued)

OTHER PUBLICATIONS

PCT International Search Report dated Sep. 7, 2010 for PCT App. Serial No. PCT/JP2010/063815.

(Continued)

*Primary Examiner* — Ryan J Severson
*Assistant Examiner* — Anh Dang
(74) *Attorney, Agent, or Firm* — Henricks, Slavin & Holmes LLP

(57) ABSTRACT

A lens holding ring 50 is held by a string-like body 40a stretched along a surface of an eyeball 1 by being supported by a plurality of cannulas 21, 22 inserted to a sclera 2, and is fixed to the surface of the eyeball 1 by a tensile stress of the string-like body 40a, and in this state, holds a surgery lens 30 on the eyeball. The lens holding ring 50 comprises a lens holder 51 including an opening 52 into which a lens is inserted, and engagement parts 57 provided at positions opposed to each other across the opening 52. Each engagement part has an engagement structure of engaging with the string-like body 40a for fixing the lens holder to the surface of the eyeball so as to interpose the lens holder therein, and has a folded part 58 on the tip of the engagement part for preventing coming-off of the string-like body.

18 Claims, 12 Drawing Sheets

(56) References Cited

U.S. PATENT DOCUMENTS

| | | |
|---|---|---|
| 2003/0109885 A1 | 6/2003 | Tano |
| 2005/0288697 A1 | 12/2005 | Tei |

FOREIGN PATENT DOCUMENTS

| | | | |
|---|---|---|---|
| JP | 2006-6605 | A | 1/2006 |
| JP | 3827229 | B2 | 9/2006 |
| JP | 2007-007332 | A | 1/2007 |
| JP | 2007-7332 | A | 1/2007 |

OTHER PUBLICATIONS

EPO Extended Search Report dated Mar. 3, 2013 for EP App. Ser. No. 10 80 9942.

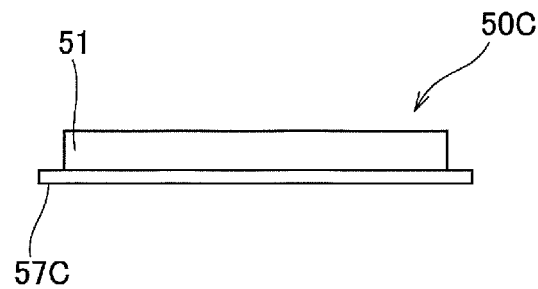
FIG. 6
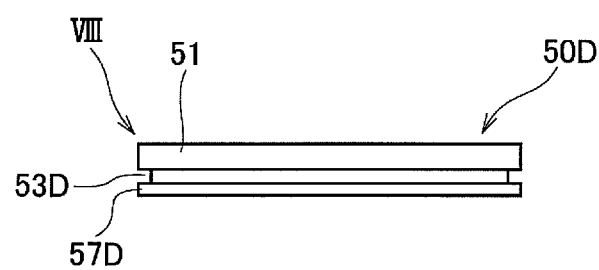
FIG. 7
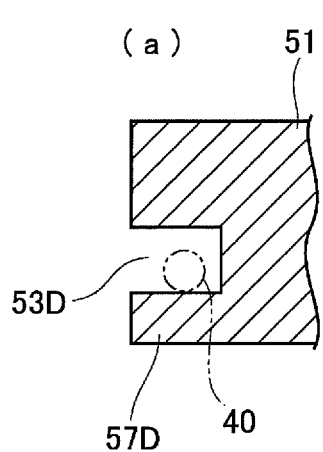 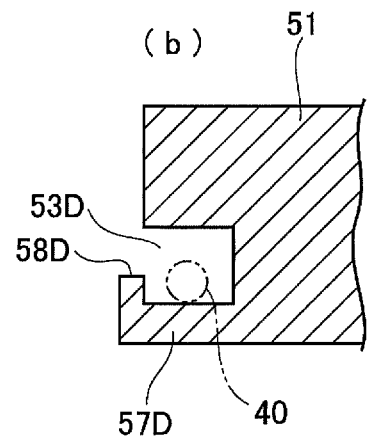
FIG. 8(a)  FIG. 8(b)

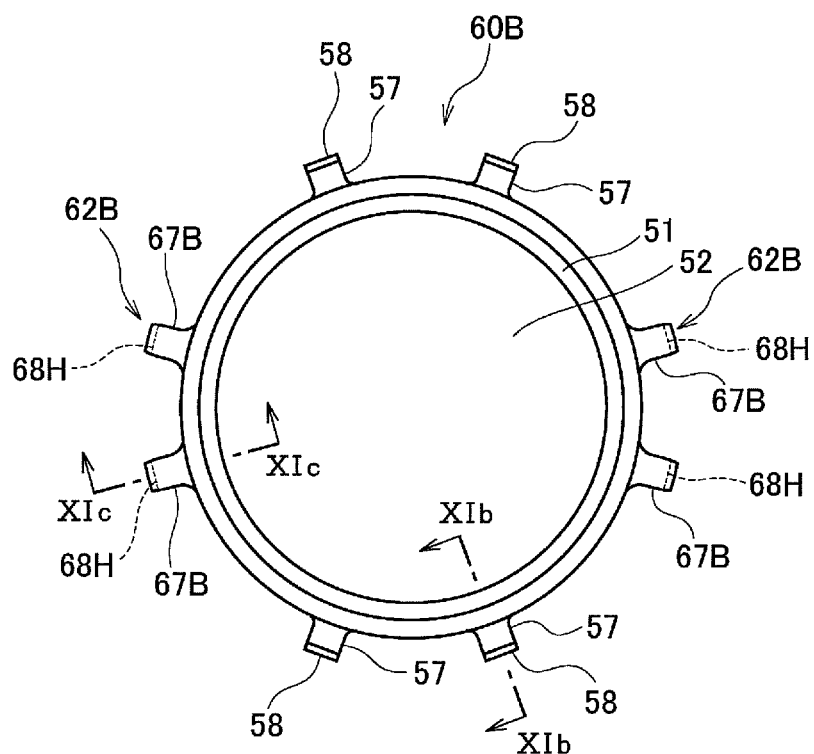
FIG. 11(a)
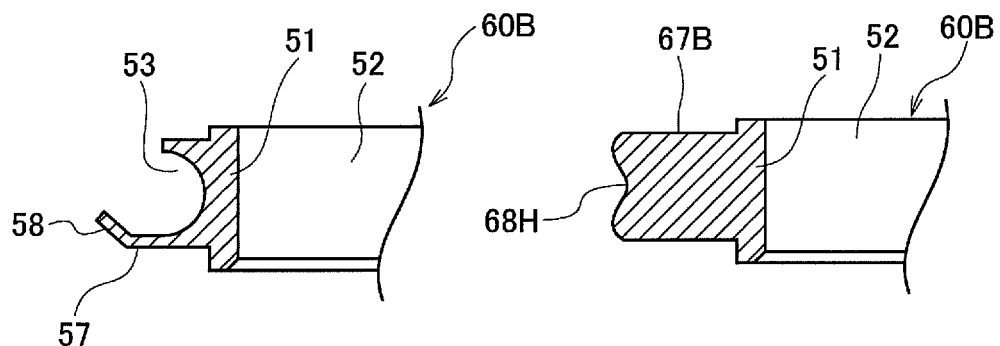
FIG. 11(b)　　　FIG. 11(c)

HOLDING DEVICE FOR CONTACT LENS FOR VITREOUS SURGERY, HOLDING DEVICE SET, AND CONTACT LENS FOR VITREOUS SURGERY, AND LENS SET

TECHNICAL FIELD

The present invention relates to a contact lens holding device for a vitreous surgery, a holding device set for holding a contact lens for a vitreous surgery on a human eyeball, which is a contact lens used for a diagnosis and a surgery of a human eyeball, and a contact lens for a vitreous surgery that can be held on the human eyeball, and a lens set.

DESCRIPTION OF RELATED ART

A vitreous surgery is usually performed by observing an inside of an eyeball, with a surgery lens (a contact lens for a vitreous surgery) placed on a cornea, after sufficiently opening eyelids of a patient who is laid on his/her back, using an eyelid opener. However, the eyeball is formed in approximately a spherical body, and therefore the surgery lens needs to be held on the eyeball.

In order to cope with this point, conventionally a ring-shaped holding device is sutured to a sclera using a surgical thread, and in this state a surgery is performed. Explanation will be given hereafter for a case of a vitreous surgery which is a typical ophthalmic surgical procedure for example, using FIG. 14, FIG. 15(a), FIG. 15(b), and FIG. 16.

In the vitreous surgery, first, as shown in FIG. 14, an upper eyelid 410 and a lower eyelid 420 of an eyeball 400 of a patient who is laid on his/her back, by vertically pulling them using an eyelid opener 510. Next, a surgery lens 550 is held on a desired position on the opened eyeball 400. However, since the eyeball 400 is approximately a spherical body, the surgery lens 550 needs to be held on the eyeball so as not to be slid down from the surface of the eyeball.

Therefore, conventionally, as shown in FIG. 14, a ring-shaped holding device 530 for a surgery lens (called a lens holding ring 530 hereafter) is sutured to a sclera 430 on the eyeball 400 (white portion of the eyeball) using a surgical thread 560.

FIG. 15(a) shows a case that the lens holding ring 530 having suture engagement parts 535 at two places, and FIG. 15(b) shows a case that the lens holding ring 530 having suture engagement parts 536, 537 at four places, is sutured to the eyeball 400, and FIG. 16 shows a cross-sectional view taken along the line XVI-XVI of FIG. 15(b) at this time.

Here, as shown in FIG. 15(a) and FIG. 15(b), the lens holding ring 530 has a larger diameter than a diameter of a cornea 431, and is held on the sclera 430. As the surgical thread 560 for suturing the lens holding ring 530 to the sclera 430, for example 5-0 dacron thread and 7-0 silk thread are used.

As shown in an example of FIG. 15(a), an operator passes the surgical thread 560 through a surgical needle, and makes it pass through the sclera 430 so as to scoop-up an upper half layer of the sclera 430 as shown in FIG. 16, and thereafter lays the surgical thread 560 on the suture engagement parts 535, to thereby suture a lens holding ring 30 to an eyeball 100.

FIG. 15(b) is an explanatory view showing an example of a suturing method that is used when the lens holding ring 530 can be attached and detached. In this case, as shown in FIG. 16, the operator passes the surgical thread 560 through the surgical needle and makes it pass through the sclera 430 so as to scoop-up the upper half layer of the sclera 430, to thereby fix suture engagement parts 536, 537 while moving around the lens holding ring 530, to thereby temporarily suture 561 the surgical thread 560 finally.

In a case of removing the lens holding ring 530, the temporary suture 561 is released, to thereby loosen the surgical thread 560 and take off the surgical thread 560 from the suture engagement parts 536, 537. Further, in a case of a re-suture, the surgical thread 560 is laid on the suture engagement parts 536, 537, and the temporary suture 561 is performed again, to fix the suture engagement parts 536, 537, then the lens holding ring 530 is re-sutured to a desired position.

As described above, when the suture of the lens holding ring 530 to the eyeball 400 is completed, as shown in FIG. 14, the operator performs intraocular surgery by inserting the surgery lens 550 into the lens holding ring 530 and inserting a scalpel into the eyeball 400, and using a vitreous cutter 570, etc., for cutting and sucking a vitreous body in the eyeball 400, and inserting an infusion 590 into the eyeball 400 for injecting perfusate of an amount corresponding to an amount of sucking the vitreous body.

In FIG. 14, an operation microscope not shown is set in an upper part of the surgery lens 550, and the surgery is executed by the operator while observing an operating field through the operation microscope and the surgery lens 550. With a progress of the surgery, when there is a necessity for observing a different operating field, the operating field is suitably moved while rotating the surgery lens 550 using a cotton swab 575 or fingers, etc. Further, the surgery lens 550 is exchanged with a lens having a different shape as needed, or the sutured position of the lens holding ring 530 is changed as described above.

The intraocular surgery is performed as described above. However, the following problem is clarified.

A first problem is that it is a laborious operation requiring close attention even by an experienced operator, to pass the surgical thread 560 through the sclera 430 using the surgical needle so as to scoop-up the upper half layer of the sclera 430. In addition, this stage is a preparatory stage of the intraocular surgery, and it is time consuming and a great disadvantage for the intraocular surgery thereafter, to impose on the operator a load of requiring a close attention in this stage, which is a great disadvantage for the intraocular surgery thereafter.

A second problem is that if the surgical needle penetrates the sclera 430 even when the close attention is paid by the experienced operator, there is a possibility that complications after surgery is developed by a damage of a tissue under the sclera.

A third problem is that even if the surgical needle does not penetrate the sclera 430, there is no difference in invading the sclera 430 by the surgical needle and the surgical thread 560.

A fourth problem is that since the lens holding ring 530 is fixed to the surface of the eyeball 400, when a surgical operation is inhibited by the lens holding ring 530 with a progress of the surgery, the lens holding ring 530 needs to be removed by cutting the surgical thread 560 every time, or releasing the temporary suture 561 and loosening the surgical thread 560, resulting in repeating the first to third problems.

For example, in a case of a triple surgery of simultaneously executing three kinds of surgeries of phacoemulsification, vitreoretinal surgery, and intraocular lens interposition surgery, the surgery is in progress in an order of (i) phacoemulsification, (ii) vitreoretinal surgery, (iii) interposition of the intraocular lens, and (iv) evacuation-replacement/endophotocoagulation, wherein in the stage of (ii) and (iv), the surgery lens 550 is required, and meanwhile in a stage of (iii), the surgery can not be executed if the surgery lens 550 and the lens holding ring 530 are sutured to the eyeball 400, and therefore when the proceeding is moved from (ii) to (iii), the surgical thread 560 needs to be cut or loosen to remove the lens holding ring 530, and when the proceeding is moved from (iii) to (iv), the lens holding ring 530 needs to be sutured again.

A fifth problem is that, since the lens holding ring 530 is fixed to the surface of the eyeball 400, and therefore as described above, a portion that is hardly observed is generated even if the surgery lens 500 is rotated or exchanged. Conventionally, in this case, observation is carried out by slightly tilting the surgery lens 550 in the lens holding ring 530. However, fine adjustment is difficult.

Therefore, in order to solve these problems, a technique of not suturing a lens holding ring to an eyeball, but connecting it to an eyelid opener, is developed (for example, see patent document 1).

As shown in FIG. 17 and FIG. 18, this technique is constituted of a lens holding ring 630 provided with an engagement part 635; an eyelid opener 510 configured to pull and open an upper eyelid 410 and a lower eyelid 420; and a string-like body 650 configured to hold the lens holding ring 630 in approximately a center of an exposed cornea and sclera, by hooking it on the eyelid opener 510 and the engagement part 635.

PRIOR ART DOCUMENT

Patent Document

Patent document 1: Patent Publication No. JP3827229

SUMMARY OF THE INVENTION

Problem to be Solved by the Invention

The problem of the technique of fixing the lens holding ring 530 by suture shown in FIG. 14 to FIG. 16 can be solved by the technique of holding the lens holding ring 630 by the eyelid opener 510 shown in FIG. 17 and FIG. 18, and this technique complies with a flow of a low invasion surgery. Therefore, this technique is widely spread in the field of the vitreous surgery.

However, the technique of holding the lens holding ring 630 by the conventional eyelid opener 510 involves a problem that an eye ground can not be observed through the surgery lens, because the eyeball can't be tilted largely when a posterior part of an intraocular eye ground is treated, and therefore the surgery lens can be properly held at a pupil position through which the inside of the eye is observed. However, when an intraocular circumferential part is treated, the eyeball is largely tilted by the operator, thereby deviating the pupil position from a center of a portion exposed by the eyelid opener, and simultaneously deviating the pupil position from the lens holding ring and the surgery lens inserted into the ring, with a result that the eye ground can not be observed through the surgery lens. Accordingly, the center of the ring is aligned with a center of the pupil by shifting the position of the lens holding ring 630. However, there is a problem that the surgery lens can't be properly held at the pupil position of the tilted eyeball, because the conventional eyelid opener 510 does not have a function of carrying out large adjustment, in terms of its performance.

An object of the present invention is to provide a holding device of a contact lens for vitreous surgery and a holding device set capable of holding a lens by fixing it to the eyeball, and capable of surely holding the lens at a pupil position even if the eyeball is moved, and capable of suppressing the problem of invasion by conventional suture to minimum, and a contact lens for vitreous surgery and a lens set capable of holding the lens on the human eyeball.

Means for Solving the Problem

In order to solve the above-described problem, the present invention has the following structures.

(1) A contact lens holding device for vitreous surgery for holding a contact lens for vitreous surgery on an eyeball, comprising:

a lens holder having an opening into which the contact lens for vitreous surgery is inserted; and engagement parts disposed at positions opposed to each other on an outer circumferential part of the lens holder across the opening;

wherein the engagement parts have an engagement structure of engaging a string-like body for fixing the lens holder to the surface of the eyeball so as to interpose the lens holder in contact with the engagement parts, respectively.

(2) The contact lens for vitreous surgery according to the aforementioned structure (1), wherein the string-like body is provided in a stretched state along the surface of the eyeball by being supported by support members fixed to a sclera.

(3) The contact lens holding device for vitreous surgery according to the aforementioned structure (2), wherein protruding pieces are provided as engaging parts, on an outer circumferential part of a ring body with the opening part in center, and a tensile stress of the string-like body placed on the protruding pieces is received by the protruding pieces, thereby transmitting a pressing stress to the ring body so as to be directed to the surface of the eyeball.

(4) The contact lens holding device for vitreous surgery according to the aforementioned structure (3), wherein the protruding pieces are provided in an inside range of an angle range in which the string-like body is brought into contact with the outer circumferential part when the ring body is held by the string-like body.

(5) The contact lens holding device for vitreous surgery according to the aforementioned structure (4), wherein a plurality of protruding pieces are provided separately from each other, inside of the angle range.

(6) The contact lens holding device for vitreous surgery according to any one of the aforementioned structures (3) to (5), wherein a groove is formed on the outer circumferential surface of the ring body, into which the string-like body is inserted when the ring body is held by the string-like body, with the protruding pieces protruded from a tip of a lower side wall of the groove, being an eyeball side in use.

(7) The contact lens holding device for vitreous surgery according to the aforementioned structure (3), wherein the protruding pieces are provided as ring-shaped protrusions continuous in a circumferential direction of the ring body.

(8) The contact lens holding device for vitreous surgery according to the aforementioned structure (7), wherein a continuous ring-shaped groove is formed in the circumferential direction of an outer circumference of the ring body, and the ring-shaped protrusions are composed of a lower side wall of both side walls of the ring-shaped groove, being an eyeball side.

(9) The contact lens holding device for vitreous surgery according to any one of the aforementioned structures (3) to (8), wherein a folded part is formed in at least a part of the tips of the protruding pieces in such a manner as being folded up or protruding upward from base sides of the protruding pieces, for preventing coming-off of the string-like body placed on the protruding pieces, from the tip end side.

(10) The contact lens holding device for vitreous surgery according to the aforementioned structure (3), wherein temporary holding parts of the string-like body are provided, for temporarily holding the parts opposed to each other across an opening of a ring in the ring-shaped string-like body, and in this state, securing a prescribed space between the string-like body and the outer circumference of the ring body and between the string-like body and a lower surface of the ring body.

(11) The contact lens holding device for vitreous surgery according to the aforementioned structure (10), wherein mutually separated projection parts, being two sets, are respectively provided as the temporary holding parts of the string-like body, at the parts opposed to each other across the opening of the outer circumferential part of the ring body, and a depression capable of securing the space by hooking the ring-shaped string-like body thereon by utilizing its elasticity, is formed on an outside surface of each projection part.

(12) The contact lens holding device for vitreous surgery according to the aforementioned structure (11), wherein the protruding pieces disposed at the positions opposed to each other across the opening of the ring body, are provided in an inside range of an angle range in which the string-like body is brought into contact with the outer circumferential part when the ring body is held by the ring-shaped string-like body, and the temporary holding parts of the string-like body, being the two sets of the projection parts, are disposed at the positions opposed to each other in a direction approximately orthogonal to a line connecting protruding pieces formed at the positions opposed to each other.

(13) The contact lens holding device for vitreous surgery according to the aforementioned structure (12), wherein a plurality of protruding pieces are provided separately from each other inside of the angle range, and meanwhile the projection parts, being the temporary holding parts of the string-like body, are constituted of protrusive pieces with approximately the same shape as the shape of the protruding piece, and rising pieces rising upward from tips of the protrusive pieces, and the depression is formed on an outside surface of each rising piece.

(14) The contact lens holding device for vitreous surgery according to the aforementioned structure (13), wherein a groove is provided on an outer circumferential surface of the ring body, into which the string-like body is inserted when the ring body is held by the string-like body, and the protruding pieces and the protrusive pieces are protruded from the tip of a lower side wall of the groove, being an eyeball side in use.

(15) The contact lens holding device for vitreous surgery according to the aforementioned structure (13) or (14), wherein the rising pieces for preventing coming-off of the string-like body placed on the protruding pieces from the tip side of the string-like body are provided on the tip of each of the protruding pieces, and the protruding pieces and the rising pieces are formed into the same shape as the shapes of the protrusive pieces and the rising pieces, being the projection parts.

(16) A contact lens holding device set for vitreous surgery, formed by a combination of the contact lens holding device for vitreous surgery and the string-like body according to any one of the aforementioned structures (1) to (15), wherein the string-like body is made of a ring-shaped elastic member capable of interposing the contact lens holding device for vitreous surgery between mutually parallel portions by hooking both ends on the support members fixed to the sclera.

(17) The contact lens holding device set for vitreous surgery, wherein cannulas are further added as the support members, to the contact lens holding device set for vitreous surgery according to the aforementioned structure (16), which are inserted to the sclera at positions opposed to each other across a cornea.

(18) A contact lens for vitreous surgery, held on an eyeball, comprising:
a lens body placed on the eyeball; and
engagement parts provided at positions opposed to each other across the lens body on an outer circumferential part of the lens body,
with the engagement parts having an engagement structure of engaging a string-like body for fixing the lens body to the surface of the eyeball so as to interpose the lens body in contact with the engagement parts, respectively.

(19) The contact lens for vitreous surgery according to the aforementioned structure (18), wherein the string-like body is provided in a stretched state along the surface of the eyeball by being supported by support members fixed to a sclera.

(20) The contact lens for vitreous surgery according to the aforementioned structure (19), wherein protruding pieces are provided as engaging parts on an outer circumferential part of a lens body, and a tensile stress of the string-like body placed on the protruding pieces is received by the protruding pieces, thereby transmitting a pressing stress to the lens body so as to be directed to the surface of the eyeball.

(21) The contact lens for vitreous surgery according to the aforementioned structure (20), wherein the protruding pieces are provided in an inside range of an angle range in which the string-like body is brought into contact with the outer circumferential part when the lens body is held by the string-like body.

(22) The contact lens for vitreous surgery according to the aforementioned structure (21), wherein a plurality of protruding pieces are provided separately from each other, inside of the angle range.

(23) The contact lens for vitreous surgery according to any one of the aforementioned structures (20) to (22), wherein a groove is provided on the outer circumferential surface of the lens body, into which the string-like body is inserted when the lens body is held by the string-like body, with the protruding pieces protruded from a tip of a lower side wall of the groove, being an eyeball side in use.

(24) The contact lens for vitreous surgery according to the aforementioned structure (20), wherein the protruding pieces are provided as ring-shaped protrusions continuous in a circumferential direction of the lens body.

(25) The contact lens for vitreous surgery according to the aforementioned structure (24), wherein a continuous ring-shaped groove is formed in a circumferential direction of an outer circumference of the lens body, and the ring-shaped protrusions are composed of a lower side wall of both side walls of the ring-shaped groove, being an eyeball side.

(26) The contact lens for vitreous surgery according to any one of the aforementioned structures (20) to (25), wherein a folded part is formed in at least a part of the tips of the protruding pieces in such a manner as being folded up or protruding upward from base sides of the protruding pieces, for preventing coming-off of the string-like body placed on the protruding pieces.

(27) The contact lens for vitreous surgery according to the aforementioned structure (20), wherein temporary holding parts of a string-like body are provided on the outer circumferential part of the lens body, for temporarily holding the parts opposed to each other across an opening of a ring in the ring-shaped string-like body when the string-like body formed in the ring-shape by an elastic member, is installed on an outer circumference of the lens body, and in this state, securing a prescribed space between the string-like body and the outer circumference of the lens body, and between the string-like body and the lower surface of the lens body.

(28) The contact lens for vitreous surgery according to the aforementioned structure (27), wherein mutually separated projection parts, being two sets, are respectively provided as the temporary holding parts of the string-like body, at the parts opposed to each other across the lens body on the outer circumferential part of the lens body, and a depression capable of securing the space by hooking the ring-shaped string-like body thereon by utilizing its elasticity, is provided outside surface of each of the projection parts.

(29) The contact lens for vitreous surgery according to the aforementioned structure (28), wherein the protruding pieces disposed at the positions opposed to each other across the lens body, are provided in an inside range of an angle range in which the string-like body is brought into contact with the outer circumferential part when the lens body is held by the ring-shaped string-like body, and the temporary holding parts of the string-like body, being the two sets of the projection parts, are disposed at the positions opposed to each other in a direction approximately orthogonal to a line connecting protruding pieces formed at the positions opposed to each other.

(30) The contact lens for vitreous surgery according to the aforementioned structure (29), wherein a plurality of protruding pieces are provided separately from each other inside of the angle range, and meanwhile the projection parts, being the temporary holding parts of the string-like body, are constituted of protrusive pieces with approximately the same shape as the shape of the protruding pieces, and rising pieces rising upward from tips of the protrusive pieces, and the depression is formed on an outside surfaces of each rising piece.

(31) The contact lens for vitreous surgery according to the aforementioned structure (30), wherein a groove is formed on an outer circumferential surface of the lens body, into which the string-like body is inserted when the lens body is held by the string-like body, and the protruding pieces and the protrusive pieces are protruded from the tip of a lower side wall of the groove, being an eyeball side in use.

(32) The contact lens for vitreous surgery according to the aforementioned structures 30 or 31, wherein a rising piece is provided for preventing coming-off of the string-like body placed on the protruding pieces from the tip side, on the tip of each protruding piece, and the protruding pieces and the rising pieces are formed into the same shape as the shapes of the protrusive pieces and the rising pieces, being the projection parts.

(33) A contact lens set for vitreous surgery, formed by a combination of the contact lens for vitreous surgery and the string-like body according to any one of the aforementioned structures (18) to (32), wherein the string-like body is made of a ring-shaped elastic member capable of interposing the contact lens for vitreous surgery between mutually parallel portions by hooking both ends on support members fixed to a sclera.

(34) A contact lens set for vitreous surgery, wherein cannulas are further added as the support members, to the contact lens set for vitreous surgery according to the aforementioned structure (33), in such a manner as being inserted to the sclera at positions opposed to each other across a cornea.

Advantage of the Invention

According to the present invention, the lens can be held on the eyeball so as to be fixed thereto, and the lens can be further surely held at a position of a pupil even if the eyeball is moved, and the problem of invasion, etc., by conventional suture, etc., can be suppressed to minimum.

Particularly, according to the aforementioned (1), the engagement parts provided on the outer circumferential part of the lens holder has the engagement structure of engaging the string-like body for fixing the lens holder to the surface of the eyeball so as to interpose the lens holder in contact with the engagement parts, respectively. Therefore, the contact lens for vitreous surgery can be fixed to a proper position on the eyeball by being supported by the support members (such as cannulas) inserted to the sclera. Accordingly, the contact lens for vitreous surgery can be held at the pupil position even when the eyeball is tilted unlike a case that it is supported by the eyelid opener, and an intraocular observation can be properly performed through the lens, even when an intraocular circumferential part is treated. Further, the string-like body for fixing the holding device can be supported by the support members (such as cannulas) which are always used in vitreous surgery. Therefore, the problem of the conventional suture can be prevented.

According to the aforementioned structure (2), the string-like body is stretched along the surface of the eyeball by being supported by the support members fixed to the sclera. Therefore, the lens holder can be easily fixed to the surface of the eyeball by utilizing the tensile stress of the string-like body.

According to the aforementioned structure (3), the lens holder is configured as the ring body having the opening in the center, and the protruding pieces are provided as the engaging parts on the outer circumferential part of the ring body, and the tensile stress of the string-like body placed on the protruding pieces is received by the protruding pieces, thereby transmitting the pressing stress to the ring body so as to be directed to the surface of the eyeball. Therefore, the lens holder can be further surely fixed to the surface of the eyeball by utilizing the tensile stress of the string-like body.

According to the aforementioned structure (4), the protruding pieces are provided in the inside range of the angle range in which the string-like body is brought into contact with the outer circumferential part when the ring body is held by the string-like body. Therefore, the string-like body stretched along the surface of the eyeball is surely engaged with the protruding pieces, and is hardly taken off therefrom.

According to the aforementioned structure (5), a plurality of protruding pieces are provided separately from each other, inside of the angle range. Therefore, the protruding pieces can be provided for stably holding the holding device by the string-like body in an efficient state.

According to the aforementioned structure (6), the groove is formed on the outer circumference of the holding device which is formed as the ring body. Therefore, the holding device can be stably held by the string-like body fitted into the groove.

According to the aforementioned structure (7), the protruding pieces are provided as the ring-shaped protrusions continuous in the circumferential direction of the ring body. Therefore, the string-like body can be engaged with the ring-shaped protrusions at arbitrary positions in the circumferential direction, and the holding device can be rotated while being fixed to the surface of the eyeball by the string-like body.

According to the aforementioned structure (8), the continuous ring-shaped groove is formed in the circumferential direction of the outer circumference of the ring body, and the lower side wall of the ring-shaped groove can be utilized as the ring-shaped protrusions to be engaged with the string-like body. Therefore, processing is facilitated at a low cost.

According to the aforementioned structure (9), the folded part is formed in at least a part of the tips of the protruding pieces in such a manner as being folded up or protruding upward from base sides of the protruding pieces.

Therefore, the holding device can be stably held by the string-like body.

According to the aforementioned structure (10), the temporary holding parts of the string-like body are provided on the outer circumferential part of the ring body. Therefore, when the ring-shaped string-like body is installed on the outer circumference of the ring body, the string-like body can be temporarily held at the opposed parts across the opening of the ring in the ring-shaped string-like body, and in this state, the prescribed space can be secured between the string-like body and the outer circumference of the ring body, and between the string-like body and the lower surface of the ring body. Accordingly, the string-like body installed on the outer circumference of the ring body can be placed on the protruding pieces formed on the outer circumference of the ring body by placing the ring body on the surface of the eyeball in a state that the string-like body is previously installed on the outer circumference of the ring body, and in this state, inserting a surgical appliance such as tweezers into a space between the string-like body and the outer circumference of the ring body, and hooking the string-like body on the support members (such as cannulas) which are previously inserted into the eyeball while stretching the opposed parts across the opening of the ring in the string-like body to outside by the inserted appliance, and the ring body (lens holder) can be surely fixed to the surface of the eyeball by pressing the ring body against the surface of the eyeball by the tensile stress of the string-like body placed on the protruding pieces.

In this operation, the space is secured between the string-like body previously installed on the outer circumference of the ring body and the outer circumference of the ring body, and the surgical appliance such as tweezers can be inserted into this space. Therefore, the string-like body can be easily hooked on the support member (such as cannulas) while being stretched by the surgical appliance such as tweezers. Further, at this time, the space is also secured between the string-like body and the lower surface of the ring body. Therefore, it is easy to handle the surgical appliance such as tweezers so that its tip is not brought into contact with the eyeball as much as possible.

According to the aforementioned structure (11), the space can be easily secured by hooking the string-like body on the depression on outside surfaces of two projection parts.

According to the aforementioned structure (12), the position where the protruding pieces are formed, and the position where the temporary holding part of the string-like body is formed are set in an orthogonal relation to each other. Therefore, the string-like body can be automatically placed on the protruding pieces only by hooking it on the support members (such as cannulas) fixed to the surface of the eyeball, thus facilitating the setting.

According to the aforementioned structure (13), the projection parts, being the temporary holding parts of the string-like body, are constituted of the protrusive pieces with approximately the same shape as the shape of the protruding pieces, and rising pieces continuously formed on the tip of the protrusive pieces. Therefore, a design and a manufacture can be facilitated.

According to the aforementioned structure (14), the groove is provided on the outer circumferential surface of the ring body, into which the string-like body is inserted when the ring body is held by the string-like body, and the protruding pieces and the protrusive pieces are protruded from the tip of the lower side wall of the groove, being the eyeball side in use. Therefore, the string-like body can be stably installed on the outer circumference of the ring body while preventing an unnecessary slippage when the ring-shaped string-like body is installed on the outer circumference of the ring body in a temporary holding stage. Further, the string-like body can be automatically hooked on the protruding pieces from the groove, when the string-like body is hooked on the support member such as cannulas from a temporary holding state.

According to the aforementioned structure (15), the rising pieces for preventing coming-off of the string-like body are provided on the tip of each protruding piece, and the protruding pieces and the rising pieces are formed into the same shape as the shapes of the protrusive pieces and the rising pieces, being the projection parts. Therefore, structures of all protrusions can be arranged in the same shape, thus facilitating the design and manufacture.

According to the aforementioned structure (16), one ring-shaped elastic member and the holding device is formed as a set. Therefore, it is easy to be handled during surgery.

According to the aforementioned structure (17), one ring-shaped elastic member and the cannulas, being the support members, are formed as a set. Therefore, it is easy to be handled during surgery.

According to the aforementioned structure (18), each engagement part has the engagement structure of engaging the string-like body for fixing the lens body to the surface of the eyeball so as to interpose the lens body in contact with the engagement parts respectively. Therefore, by supporting the string-like body by the support members (such as cannulas) inserted to the sclera, the contact lens for vitreous surgery can be fixed to a proper position on the eyeball. Accordingly, unlike a case that the string-like body is supported by the eyelid opener, the contact lens for vitreous surgery can be held at the pupil position even when the eyeball is tilted, and the intraocular observation can be properly carried out through the lens even when the intraocular circumferential part is treated. Further, the string-like body for fixing the lens can be supported by the support members (such as cannulas) which are always used for the vitreous surgery. Therefore, the problem by conventional suture can be prevented. Further, the engagement parts are provided for hooking the string-like body on the lens itself, and therefore the ring-shaped holding device (lens holding ring) can be eliminated, and the number of appliances required for the surgery can be reduced.

According to the aforementioned structure (19), the string-like body is provided in a stretched state along the surface of the eyeball by being supported by the support members fixed to the sclera. Therefore, the contact lens for vitreous surgery can be easily fixed on the surface of the eyeball by utilizing the tensile stress of the string-like body.

According to the aforementioned structure (20), the protruding pieces are provided as the engaging parts on the outer circumferential part of the lens body, and the tensile stress of the string-like body placed on the protruding pieces is received by the protruding pieces, thereby transmitting the pressing stress to the lens body so as to be directed to the surface of the eyeball. Therefore, the lens can be surely fixed to the surface of the eyeball by utilizing the tensile stress of the string-like body.

According to the aforementioned structure (21), the protruding pieces are provided in the inside range of the angle range in which the string-like body is brought into contact with the outer circumferential part when the lens body is held by the string-like body. Therefore, the string-like body stretched along the surface of the eyeball is surely engaged with the protruding pieces, and the coming-off of the string-like body hardly occurs.

According to the aforementioned structure (22), a plurality of protruding pieces are provided separately from each other, inside of the angle range. Therefore, the protruding pieces can be provided for stably holding the holding device by the string-like body in an efficient state.

According to the aforementioned structure (23), the groove into which the string-like body is inserted, is provided on the outer circumferential surface of the lens body. Therefore, the lens can be stably held by the string-like body fitted into the groove.

According to the aforementioned structure (24), the protruding pieces are provided as ring-shaped protrusions continuous in the circumferential direction of the lens body. Therefore, the string-like body can be engaged with the ring-shaped protrusions at arbitrary positions in the circumferential direction, and the lens can be rotated while being fixed to the surface of the eyeball by the string-like body.

According to the aforementioned structure (25), the continuous ring-shaped groove is formed in a circumferential direction of the outer circumference of the lens body, and the lower side wall of the ring-shaped groove can be utilized as the ring-shaped protrusion with which the string-like body is engaged. Therefore, processing is facilitated and a cost reduction is achieved.

According to the aforementioned structure (26), the folded part is formed in at least a part of the tips of the protruding pieces in such a manner as being folded up or protruding upward from the base sides of the protruding pieces. Therefore, the lens can be stably held by the string-like body.

According to the aforementioned structure (27), the temporary holding parts of the string-like body are provided on the outer circumferential part of the lens body. Therefore, the string-like body can be temporarily held at the parts opposed to each other across the opening of the ring in the ring-shaped string-like body when the ring shaped string-like body is installed on the outer circumference of the lens body, and in this state, a prescribed space can be secured between the string-like body and the outer circumference of the lens body, and between the string-like body and the lower surface of the lens body, respectively. Accordingly, the string-like body installed on the outer circumference of the ring body can be placed on the protruding pieces formed on the outer circumference of the ring body by placing the lens body on the surface of the eyeball in a state that the string-like body is previously installed on the outer circumference of the lens body, and in this state, inserting a surgical appliance such as tweezers into the space between the string-like body and the outer circumference of the lens body, and hooking the string-like body on the support members (such as cannulas) which are previously inserted into the eyeball while stretching the opposed parts across the opening of the ring in the string-like body to outside by the inserted appliance, and the lens body can be surely fixed to the surface of the eyeball by pressing the lens body against the surface of the eyeball by the tensile stress of the string-like body placed on the protruding pieces.

In this operation, the space is secured between the string-like body previously installed on the outer circumference of the ring body and the outer circumference of the lens body, and the surgical appliance such as tweezers can be inserted into the space. Therefore, the string-like body can be easily hooked on the support members (such as cannulas) while being stretched by the surgical appliance such as tweezers. Further, at this time, the space is also secured between the string-like body and the lower surface of the lens body. Therefore, it is easy to handle the surgical appliance such as tweezers so that its tip is not brought into contact with the eyeball as much as possible.

According to the aforementioned structure (28), the space can be easily secured by hooking the string-like body on the depression on the outside surfaces of two projection parts.

According to the aforementioned structure (29), the position where the protruding pieces are provided, and the position where the temporary holding parts of the string-like body, are set in a relation orthogonal to each other. Therefore, the string-like body can be automatically placed on the protruding pieces only by hooking both ends of the string-like body which come off from the temporary holding part of the string-like body, on the support members (such as cannulas) fixed to the surface of the eyeball, thus facilitating the setting.

According to the aforementioned structure (30), the projection parts, being the temporary holding parts of the string-like body, are composed of the protrusive pieces with approximately the same shape as the shape of the protruding pieces, and rising pieces continuously formed on the tip of the protrusive pieces. Therefore, a design and a manufacture can be facilitated.

According to the aforementioned structure (31), the groove is formed on the outer circumferential surface of the lens body, into which the string-like body is inserted when the lens body is held by the string-like body, and the protruding pieces and the protrusive pieces are protruded from the tip of the lower side wall of the groove, being the eyeball side in use. Therefore, the string-like body can be stably installed on the outer circumference of the ring body while preventing the unnecessary slippage when the ring-shaped string-like body is installed on the outer circumference of the ring body in a temporary holding stage. Further, the string-like body can be automatically hooked on the protruding pieces from the groove, when the string-like body is hooked on the support member such as cannulas from the temporary holding state.

According to the aforementioned structure (32), the rising pieces are provided for preventing coming-off of the string-like body placed on the protruding pieces from the tip side, on the tip of each protruding piece, and the protruding pieces and the rising pieces are formed into the same shape as the shapes of the protrusive pieces and the rising pieces constituting the projection parts as the temporary hooding parts of the string-like body. Therefore, structures of all protrusions can be arranged in the same shape, thus facilitating the design and manufacture.

According to the aforementioned structure (33), one ring-shaped elastic member and the contact lens for vitreous surgery are formed as a set, which is easy to be handled during surgery.

According to the aforementioned structure (34), one ring-shaped elastic member, the contact lens for vitreous surgery, and cannulas, being the support members, are formed as a set, which is easy to be handled during surgery.

BRIEF DESCRIPTION OF THE DRAWINGS

FIG. 6 is a side view of the lens holding ring according to other embodiment of the present invention.

FIG. 7 is a side view of the lens holding ring according to further other embodiment of the present invention.

FIGS. 8(a) and 8(b) are expanded cross-sectional views showing each example of a VIII part of FIG. 7.

FIG. 11 is a plan view of the lens holding ring according to further another embodiment of the present invention, FIG. 11(b) is an expanded cross-sectional view taken along the line XIb-XIb of FIG. 11(a), and FIG. 11(c) is an expanded cross-sectional view taken along the line XIc-XIc of FIG. 11(a).

DETAILED DESCRIPTION OF THE INVENTION

Embodiments of the present invention will be described hereafter, with reference to the drawings.

Figure 1A:
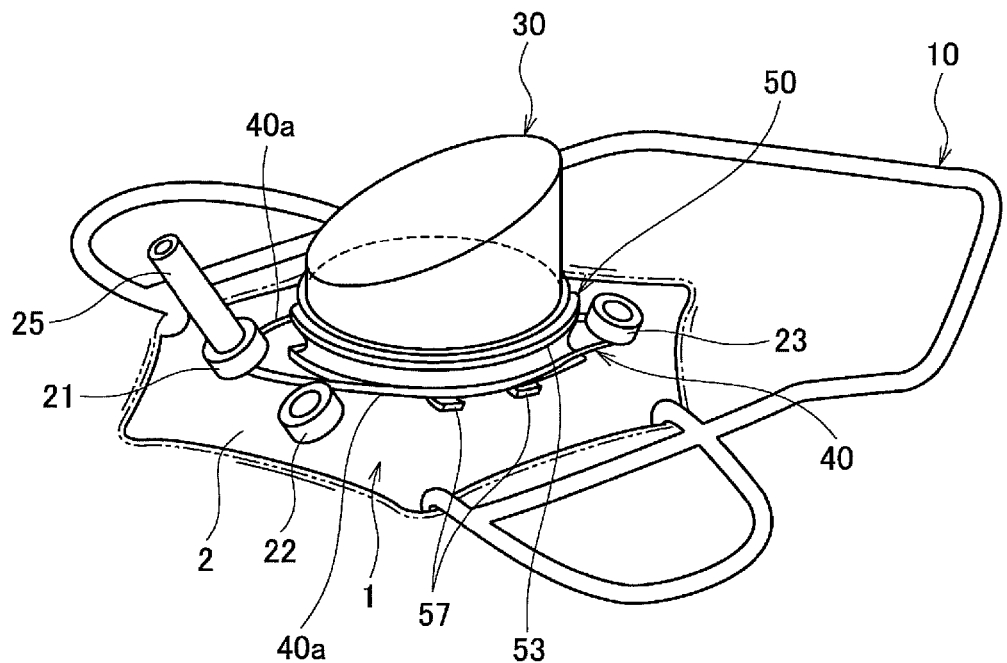
FIG. 1(a) is a perspective view showing a state that a vitreous surgery is performed using a holding device set of a contact lens for vitreous surgery according to an embodiment of the present invention.
Figure 1B:
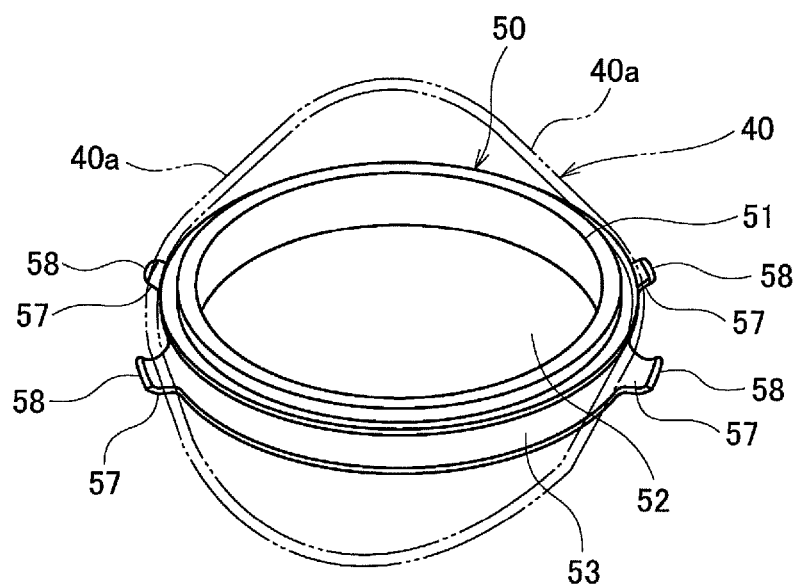
FIG. 1(b) is a perspective view showing a lens holding ring (holding device) and a rubber band (string-like body made of a ring-shaped elastic member), being a basic element of the holding device set.

In recent years, a surgical form such as minimally invasive surgery with a small incision has been spread in a vitreous surgery, and a surgery of 25 gauge (diameter: 0.5 mm) or 23 gauge (diameter: 0.65 mm) using cannulas is performed in many cases. Conventionally, conjunctiva is peeled to expose the sclera for suturing a lens holding ring (holding device) and directly inserting an appliance with a thickness of 20 gauge (diameter: 0.9 mm). However, in the vitreous surgery of 25, 23 gauge in recent years, for example as shown in FIG. 1, cannulas 21, 22, 23 passing through conjunctiva and sclera are directly set in orbiculus ciliaris at a position of 3 to 4 mm outside a corneal limbus by transconjunctival operation without peeling the conjunctiva. Designation mark 21 in FIG. 1 indicates a cannula for perfusion to which a perfusion tube 25 is connected, and designation mark 22 indicates a cannula used as a lens guide, and designation mark 23 indicates a cannula into which a treatment appliance is inserted.

In this embodiment, two cannulas that exist at opposed positions across a cornea 6 (FIG. 2) out of three cannulas 21 to 23 inserted into the eyeball 1 are used, not by a conventional eyelid opener 10 or not by a conventional suture, to thereby support a lens holding ring (holding device) 50 for holding a contact lens 30 for vitreous surgery. The lens holding ring 50 is supported by the cannulas 21, 23 through a string-like body 40, and is used as a set together with the string-like body 40. Further, the string-like body 40 and the cannulas 21, 23 are used as a set as needed.

Figure 2:
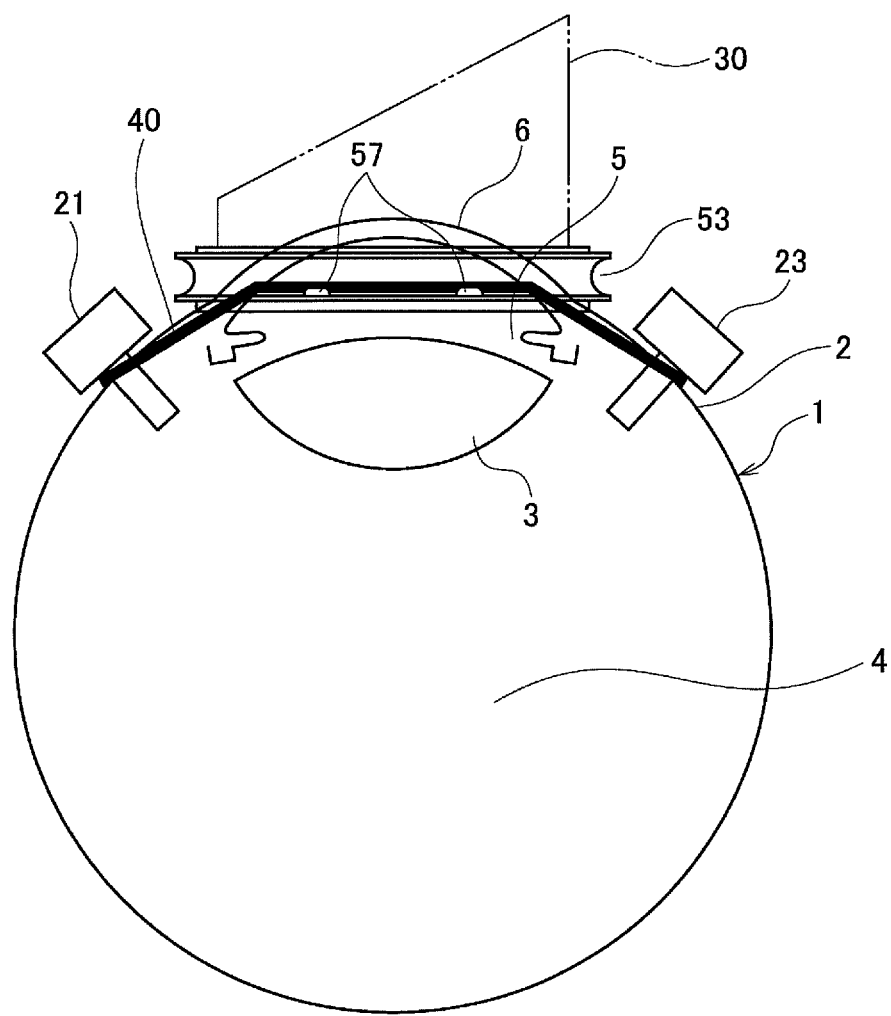
FIG. 2 is a cross-sectional view showing a state that the vitreous surgery is performed using the holding device set.
Figure 3A:
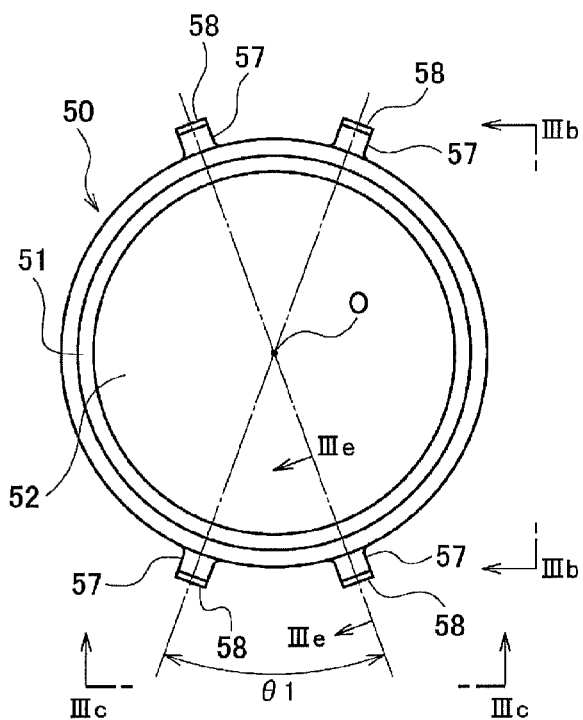
FIG. 3(a) is a plan view of the lens holding ring shown in FIG. 1(b) viewed from above.
Figure 3B:
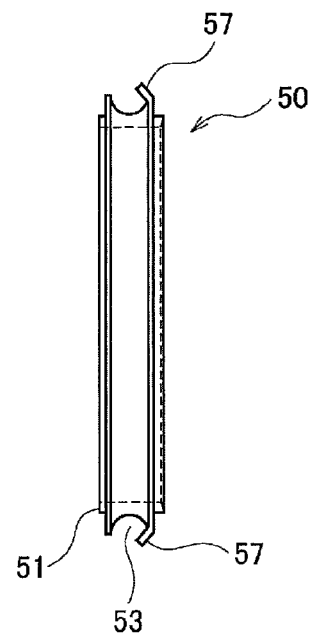
FIG. 3(b) is a view taken along the line IIIb-IIIb of FIG. 3(a)
Figure 3C:
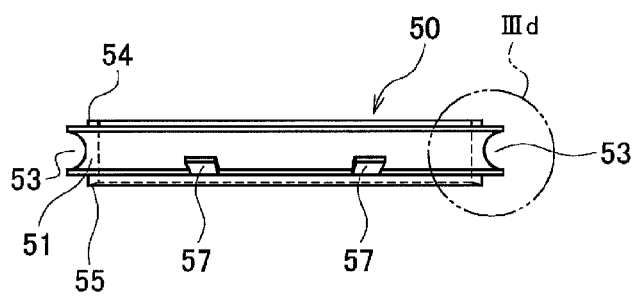
FIG. 3(c) is a view taken along the line IIIc-IIIc of FIG. 3(a)
Figure 3D:
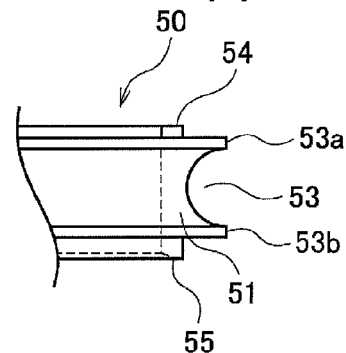
FIG. 3(d) is an expanded view of IIId circle portion of FIG. 3(c)
Figure 3E:
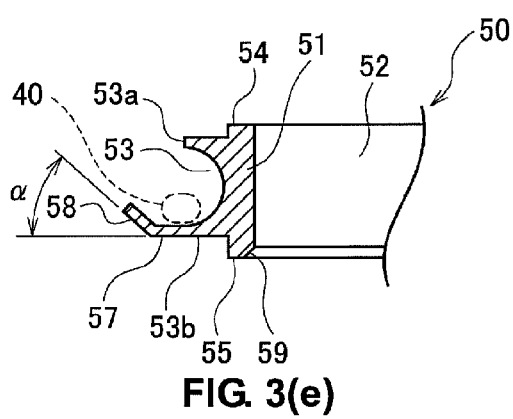
FIG. 3(e) is a cross-sectional view taken along the line IIIe-IIIe of FIG. 3(a).

In FIG. 1 and FIG. 2, designation mark 1 indicates an eyeball, 2 indicates sclera, 3 indicates a crystalline lens, 4 indicates a vitreous body, 5 indicates a pupil, 6 indicates a cornea, and 10 indicates an eyelid opener, wherein three cannulas (support members) 21 to 23 are previously inserted into the sclera 2 of the eyeball 1 which is exposed by pulling upper and lower eyelids by the eyelid opener 10. Designation mark 50 indicates a metal or resin lens holding ring (holding device) with a diameter formed slightly larger than a diameter of the cornea 6, 40 indicates a string-like body for holding the lens holding ring 50 around the cornea 6, 30 indicates a contact lens for vitreous surgery (surgery lens) inserted into the lens holding ring 50 and placed on the cornea 6 of the eyeball 1.

The string-like body 40 is a rubber band made of one silicone rubber (ring-shaped elastic member), and is laid along a surface of the eyeball between the cannulas 21 and 23 with its tensile stress, by extending the ring and hooking its both ends in an underhead part of the cannulas 21, 23. Then, an outer circumferential part of the lens holding ring 50 is interposed between mutually paralleled opposed two string bodies 40a, and the lens holding ring 50 is fixed to a fixed position on the eyeball 1 (on the cornea 6) by being pressed against the surface of the eyeball 1 by the tensile stress of two string bodies 40a. The rubber band as the string-like body 40 used here has a diameter of about 10 to 20 mm, and a thickness of about 0.1 to 0.8 mm. Above all, the rubber band with a diameter of 12 to 14 mm, and a thickness of 0.2 to 0.5 mm is preferably used. However, the rubber band for children's use has preferably a dimension of about ⅔ of the aforementioned dimension.

As shown in FIG. 1(b) and FIG. 3(a) to FIG. 3(e), the lens holding ring 50 has a ring-shaped ring body (lens holder) 51 including an opening 52 in the center, into which a surgery lens 30 is inserted; and a plurality of protruding pieces (engagement parts) 57 protrusively formed on an outer circumferential part of the ring body 51. The ring body 51 has an inner diameter of about 10 mm to 13 mm, and an outer diameter of about 12 to 15 mm, and a thickness of about 2 mm. Projected ring parts 54, 55 having a small diameter with an outer diameter set to be smaller than a center part of the thickness, are provided on upper and lower surfaces in the center part of the thickness of the ring body 51 having a larger outer diameter, and a chamfered part 59 suited to a shape of the eyeball 1 is provided on an inner circumference of the lower side projected ring part 55. Note that the inner circumferential surface of the ring body 51 is formed as a smooth continuous cylindrical surface, including the inner circumferential surface of the projected ring parts 54, 55 which have a small diameter.

Two protruding pieces 57 for receiving the tensile stress of the string-like body 40a, are provided at opposed two positions across a center O of a circular opening 52 of the ring body 51. These protruding pieces 57 are parts that function as the engagement parts for transmitting a pressing stress to the ring body 51 toward the surface of the eyeball 1.

These protruding pieces are formed protrusively on the outer circumferential part of the ring body 51, and a folded part 58 is formed on a tip of each protruding piece 57 in such a manner as being folded up or protruding upward from a base side of the protruding piece, for preventing coming-off of the string-like body 40a placed on the protruding piece 57, from the tip end side. A folding angle α of the folded part 58 is desirably set to about 45°. Further, a groove 53 of semi-circle in cross section into which the string-like body 40a is inserted when the ring body 51 is interposed between two string bodies 40a, is formed over entire part of the outer circumference of the ring body 51. By forming such a groove 53 on the outer circumferential surface, the upper side wall 53a and the lower side wall 53b are protruded radially outward from an inner bottom of the groove 53. Then, in this embodiment, the protruding piece 57 is formed protrusively on the tip of the lower side wall 53b, being the eyeball side 1 in use.

Figure 4:
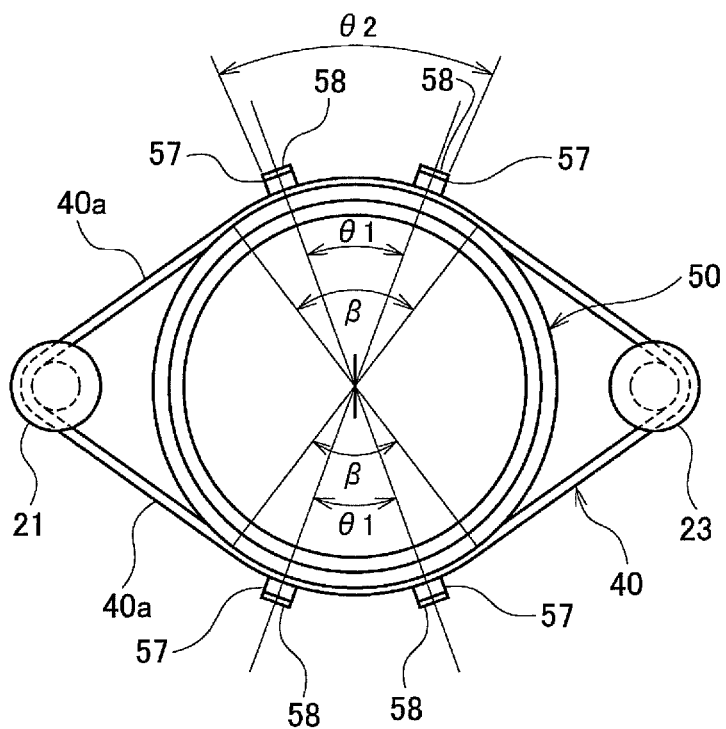
FIG. 4 is a plan view for describing a position of a protruding piece of the lens holding ring.

Further, an opening angle θ1 of two protruding pieces 57 provided at each sides opposed across the opening 52, is about 40°. As shown in FIG. 4, the protruding pieces 57 may be provided inside range of the angle range β in which the string-like body 40a is brought into contact with the outer circumferential part when the ring body 51 is interposed between two string bodies 40a, and specifically angle θ2 from an outside edge of one of the protruding pieces 57 to an outside edge of the other protruding piece 57 is in a range of β.

Figure 5:
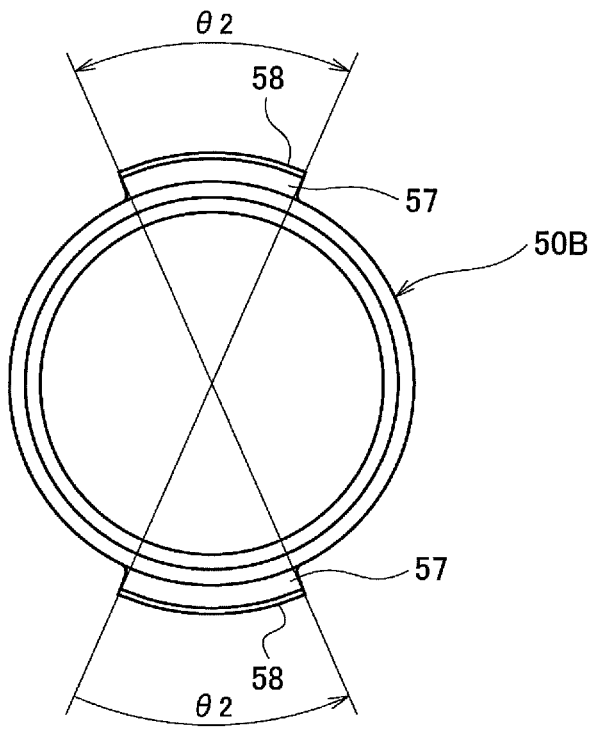
FIG. 5 is a plan view showing a modified example of the protruding piece.

The lens holding ring 50 of this embodiment shows a case that two protruding pieces 57 are independently provided so as to be separated from each other. However, one protruding piece 57 may also be provided at each side of the opposed both sides so as to be continuously formed in a range of angle θ2, like the lens holding ring 50B of FIG. 5.

When the surgery lens 30 is held using the lens holding ring 50 with this structure, first, the rubber band (string-like body) 40 is laid on the cannulas 21, 23 which are previously inserted. Subsequently, the lens holding ring 50 is placed on the eyeball 1, and each of the mutually opposed two string bodies 40a formed by the laid rubber band 40 is placed on two protruding pieces 57 at one side of the lens holding ring 50, and on the two protruding pieces 57 at the other side thereof. Thus, the lens holding ring 50 can be held on the eyeball 1, by the tensile stress of the string-like body 40a. Subsequently, the lens 30 can be held at a fixed position by inserting the surgery lens 30 into the lens holding ring 50 in this state.

Thus, the lens holding ring 50 holding the surgery lens 30 is fixed to a proper position on the eyeball 1, by supporting it by the cannulas 21, 23 inserted into the sclera. Therefore, the surgery lens 30 can be held at a position of the pupil 5 even when the eyeball 1 is largely tilted, unlike a conventional case that the surgery lens 30 is supported by the eyelid opener 10. Accordingly, intraocular observation can be properly performed through the surgery lens 30, even when an intraocular circumferential part is observed, thus making it possible to perform smooth surgery. Further, the rubber band 40 for fixing the lens holding ring 50 can be supported by the cannulas 21, 23 which are always used during vitreous surgery, and therefore a problem caused by conventional suture can be avoided.

Particularly, the folded part 58 is formed on the tip of each protruding piece 57 which is provided as the engagement part, for preventing coming-off of the string-like body 40a. Therefore, the lens holding ring 50 can be stably held by the string-like body 40a. Further, the groove 53 into which the string-like body 40a is inserted, is provided on the outer circumference of the ring body 51. Therefore, a holding force can be given properly to the lens holding ring 50 by the string-like body 40a which is fitted into the groove 53, and therefore the lens holder 50 can be stably held. Further, the protruding pieces 57 provided as the engagement parts, are provide inside range of the angle range β in which the string-like body 40a is brought into contact with the outer circumferential part when the ring body 41 is interposed between the string bodies 40a. Therefore, the string bodies 40a stretched along the surface of the eyeball 1, are surely engaged with the protruding pieces 57, and are hardly come off. Further, a plurality of protruding pieces 57 are provided inside of the angle range β so as to be separated from each other, and therefore the protruding pieces 57 can be provided in an efficient state for stably holding the lens holding ring 50 by the string bodies 40a.

Note that the aforementioned embodiment shows a case that each protruding pieces having an independent shape is formed protrusively on the outer circumference of the ring body 51. However, a protruding piece 57C as shown in FIG. 6 may also be provided as a ring-shaped protrusion continuous in a circumferential direction of the ring body 51.

Further, a ring-shaped groove 53D continuous in the circumferential direction is formed on the outer circumference of the ring body 51, like the lens holding ring 50D shown in FIG. 7 and FIG. 8(a) and FIG. 8(b), and a lower side wall 57D, being the eyeball side, of both side walls of the ring-shaped groove 53D may be utilized as the ring-shaped protrusion (protruding piece 57D). At this time, a size of a sectional surface of the ring-shaped groove 53D needs to be the size that allows the rubber band 40 to be put therein.

Further, in order to prevent the rubber band 40 from coming off from the ring-shaped groove 53D into which it is fitted once, as shown in FIG. 8(b), a folded part 58D protruded upward may be provided on the tip of the ring-shaped protrusion (protruding piece 57D). However, the folded part 58D in this case is preferably provided only in a part in the circumferential direction (similar angle range as θ2 of FIG. 4) in consideration of a hooking performance of the string-like body 40. Note that the folded part 58D can be provided similarly in a case of the lens holding ring 50C of FIG. 6 as well.

The lens holding ring according to another embodiment facilitating the setting on the eyeball will be described next.

Figure 9A:
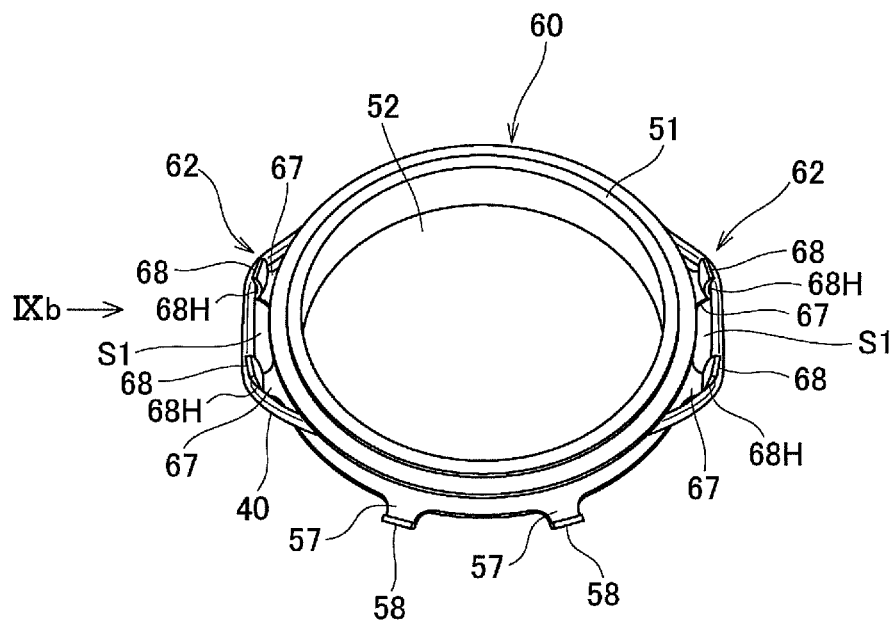
FIG. 9(a) is a perspective view of a holding device (lens holding ring) of the contact lens for vitreous surgery according to another embodiment of the present invention in a state that the rubber band (string-like body made of the ring-shaped elastic member) is installed on the outer circumference of the holding device.

FIG. 9 is a block diagram of a lens holding ring 60 according to this embodiment, wherein (a) is a perspective view showing a state that the rubber band (string-like body) 40 is installed on the outer circumference of this lens holding ring 60, and (b) is an expanded side view of IX portion of (a) indicated by arrow IX, showing a state that the rubber band 40 is stretched to outside by inserting tweezers 70 into a space secured inside of the rubber band 40 by a string-like body temporary holding part 62. Further, FIG. 10 is a block diagram of the lens holding ring shown in FIG. 9(a), wherein (a) is a plan view viewed from above, and (b) is a view taken along the line Xb-Xb of (a), (c) is a view taken along the line Xc-Xc of (a), (d) is an expanded view of Xd circle portion, (e) is an expanded cross-sectional view taken along the line Xe-Xe of (a), and (f) is an expanded cross-sectional view taken along the line Xf-Xf of (a).

The lens holding ring 60 of this embodiment includes sting body temporary holding parts 62 for temporarily holding the parts opposed to each other across the opening of a ring in the rubber band 40 when the rubber band 40 is installed on the outer circumference of the ring body 51 as shown in FIG. 9, on the outer circumferential part of the ring body (lens holder) 51 of the lens holding ring shown in FIG. 1 to FIG. 4. When an example is given regarding this structure, the string-like body temporary holding parts 62 for temporarily holding two parts opposed to each other in a diameter direction, are provided in the rubber band 40. In this embodiment, the string-like body temporary holding parts 62 with this form will be described. Note that other structure is the same as the structure of the lens holding ring 50 shown in FIG. 1 to FIG. 4, and therefore the same signs and numerals are assigned to the same element, and overlapped explanation is omitted.

Figures 10A, 10B:
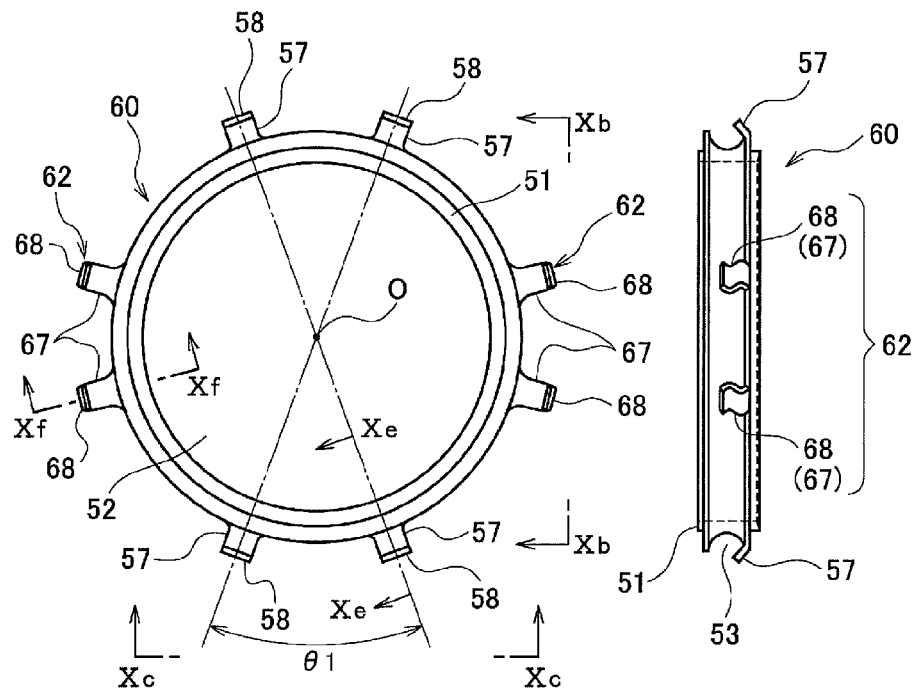
FIG. 10(a) is a plan view of the lens holding ring shown in FIG. 9(a) view viewed from above.
FIG. 10(b) is a view taken along the line Xb-Xb of FIG. 10(a)

According to the string-like body temporary holding parts 62 with this structure, when the string-like body is temporarily held by hooking the rubber band 40 on the string-like body temporary holding parts 62, prescribed space S1 and S2 can be secured between the rubber band 40 and the ring body 51, and between the rubber band and a lower surface (surface abutted on the eyeball) of the ring body 51, respectively, and as shown in FIG. 10(a), the temporary holding parts 62 of the string-like body are disposed at positions opposed to each other in a direction approximately orthogonal to a line connecting protruding pieces 57 formed at the positions opposed to each other.

Figures 10C, 10D:
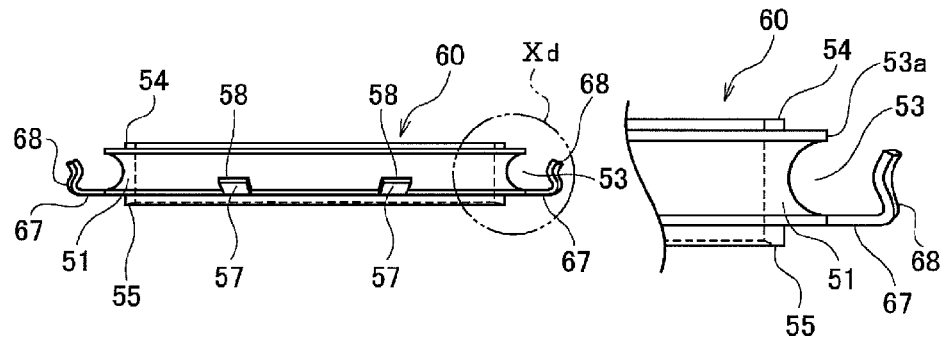
FIG. 10(c) is a view taken along the line Xc-Xc of FIG. 10(a)
FIG. 10(d) is an expanded view of Xd circle portion of FIG. 10(c)
Figures 10E, 10F:
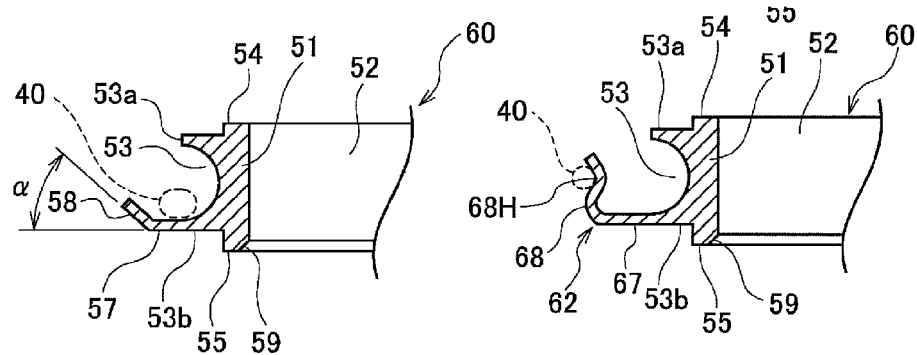
FIG. 10(e) is an expanded cross-sectional view taken along the line Xe-Xe of FIG. 10(a)
FIG. 10(f) is an expanded cross-sectional view taken along the line Xf-Xf of FIG. 10(a).

Each string-like body temporary holding part 62 in this case, is composed of mutually separated projection parts, being two sets. Each projection part in the string-like body temporary holding part 62, is composed of a protruding piece 67, and a rising piece 68 rising upside from the tip of the protruding piece 67. Note that the protruding piece 67 has approximately the same shape as the shape of the protruding piece 57 as described above. Wherein, each projection part constituting the string-like body temporary holding part 62, is formed into a shape of bending a strip plate as shown in FIG. 10(b) to (d). Then, as shown in FIG. 10(f), a depression 68H for securing the aforementioned spaces S1, S2 by hooking the rubber band 40, is provided on the outside surface of the rising piece 68. The depression 68H is formed in a groove shape along the circumference direction of the ring body 51. Note that similarly to the protruding piece 57, the protrusive piece 67 forming the projection part is provided protrusively on the tip of the lower side wall 53b of the groove 53 of the semi-circle in cross section on the outer circumferential surface of the ring body 51.

Note that unlike the string-like body temporary holding part 62 described here, and as another embodiment of the folded part 58 shown in FIG. 10(e), the folding angle α of the folded part 58 may be set to approximately 90°.

An action of the lens holding ring 60 shown in FIG. 9 and FIG. 10, will be described next.

Figure 9B:
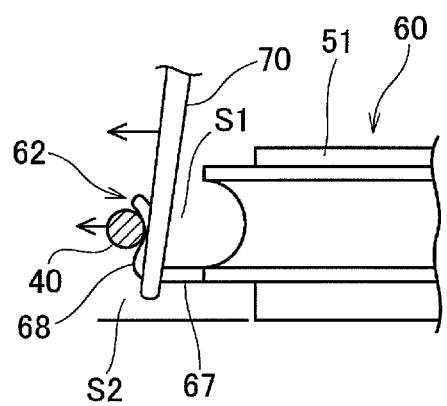
FIG. 9(b) is an expanded side view of FIG. 9(a) shown by arrow IX, showing a state that the rubber band is stretched to outside by inserting tweezers into a space secured inside of the rubber band by the temporary holding parts of the string-like body.

The lens holding ring 60 is capable of temporarily holding the parts opposed to each other across the opening of the ring in the rubber band 40, by the temporary holding part 62 of the string-like body, when the rubber band 40 is installed on the outer circumference of the ring body 51. Namely, the rubber band 40 can be temporarily held on the outer circumference of the ring body 51, by hooking the rubber band 40 on the depressions on the outside surfaces of two projection portions which constitute the string-like temporary holding parts 62 (depressions on the outside surfaces of the rising pieces 68H). In addition, in a state of temporarily holding the rubber band 40, as shown in FIG. 9(b), prescribed spaces S1, S2 can be secured respectively between the rubber band 40 and the outer circumference of the ring body 51, and between the rubber band 40 and the lower surface of the ring body 51 (surface in contact with the surface of the eyeball). The space S1 in the former case is about 0.5 mm, and for example is the space into which the tip of a surgical appliance such as tweezers 70 can be inserted. Further, the space S2 in the latter case is the space preventing the tip of the tweezers 70, etc., from strongly touching on the surface of the eyeball when the tip of the tweezers, etc., is hooked on the inner circumferential side of the rubber band 40.

Accordingly, as described above, the ring body 51 is placed on the surface of the eyeball in a state that the rubber band 40 is previously installed on the outer circumference of the ring body 51, and in this state, as shown in FIG. 9(b), the surgical appliance such as tweezers, etc., is inserted into the space S1 between the rubber band 40 and the outer circumference of the ring body 51, and the rubber band 40 is hooked on the support members (such as cannulas) 21, 23 which are previously inserted into the eyeball while stretching to outside the parts opposed to each other across the opening of the ring in the rubber band 40 (namely two parts opposed in the diameter direction of the rubber band 40), to thereby place the rubber band 40 installed on the outer circumference of the ring body 51, on the protruding pieces 57 provided on the outer circumference of the ring body 51, and with the tensile stress of the rubber band 40 placed on the protruding pieces 57, the ring body 51 is pressed against the surface of the eyeball, so that the ring body (lens holder) can be surely fixed on the eyeball.

During this operation, the space S1 is secured between the rubber band 40 previously installed on the outer circumference of the ring body 41 and the outer circumference of the ring body 51, so that the surgical appliance such as tweezers 70, etc., can be inserted into the space S1. Therefore, the rubber band 40 can be easily hooked on the support members (such as cannulas) 21, 23 while being stretched by the surgical appliance such as tweezers 70, etc. Further, at this time, the space S2 is also secured between the rubber band 40 and the lower surface of the ring body 51, and therefore it is easy to handle the tip of the surgical appliance such as tweezers 70, etc., so as to prevent it from touching on the eyeball as much as possible. Therefore, a risk of scratching the eyeball (particularly cornea) by the surgical appliance and the ring body 51 itself, can be reduced during setting the ring body 51. Further, since a setting time of the ring body 51 itself can be shortened, load added on both a patient and an operator can be reduced.

When the lens holding ring 50 shown in FIG. 1 to FIG. 4 is set on the eyeball, the following method is employed. Namely, first, the rubber band 40 is laid on two support members (such as cannulas and trocars) 21, 23, and thereafter the ring body 51 is placed on the surface of the eyeball while opening a narrow space of mutually parallel portions of the rubber band 40, so that the rubber band 40 is placed on the protruding pieces 57 provided on the outer circumference of the ring body 51. In this case, the operation is performed while clipping the rubber band 40 in a stretched state with tensile stress on the surface of the eyeball. Such a labor can be solved by the lens holding ring 60 of this embodiment. Further, when the rubber band 40 is clipped, chance or time of touching on the surface of the eyeball by the surgical appliance such as tweezers 70, etc., can be reduced, and therefore the risk of scratching the eyeball can be suppressed.

Further, according to the lens holding ring 60 of this embodiment, the temporary holding parts 62 of the string-like body are formed by two projection parts. Therefore, the spaces S1, S2 can be easily automatically secured only by hooking the rubber band 40 on the depressions 68H on the outside surfaces of two projection parts.

Further, the position where each protruding piece 57 is provided and the position where each temporary holding part 62 of the string-like body is provided, are set in a relation of being orthogonal to each other. Therefore, only by hooking both ends of the rubber band 40 unfastened from the temporary holding part 62 of the string-like body, on the support members (such as cannulas) 21, 23 fixed on the eyeball, the rubber band 40 can be automatically placed on the protruding piece 57, and setting of the lens holding ring 60 can be facilitated. Further, by forming the groove 53 on the outer circumference of the ring body 51, the rubber band 40 can be stably installed on the outer circumference of the ring body 51 while preventing an unwanted slippage, when the rubber band 40 is mounted thereon in a temporary holding stage. In addition, even when the rubber band 40 is hooked on the support members 21, 23 such as cannulas from the temporary holding state, the rubber band 40 can be automatically smoothly slid and hooked on the surface of each protruding piece 57 from the inside of the groove 53.

Further, in this embodiment, each projection part constituting the temporary holding part 62 of the string-like body, is composed of the protruding piece 67 with approximately the same shape as the shape of the protruding piece 57, and the rising piece formed continuously on the tip of the rising piece 67, and therefore design and manufacture can be facilitated.

The lens holding ring of this embodiment, which is a modified example of the lens holding ring shown in FIG. 9 and FIG. 10, will be described next.

FIG. 11 is a block diagram of the lens holding ring according to another embodiment of the present invention, wherein (a) is a plan view of this ring, (b) is an expanded cross-sectional view taken along the line XIb-XIb of (a), and (c) is an expanded cross-sectional view taken along the line XIc-XIc of (a).

In the lens holding ring 60B of this embodiment, the shape of the projection part 67B forming the temporary holding part 62B of the string-like body is not configured to bend a band plate as shown in FIG. 9 and FIG. 10, but is formed simply as a small block-shaped protrusive part having approximately a rectangular shape in cross section, with depression 68H formed on the outside surface thereof. In this case, there is an advantage that the manufacture is facilitated owing to its simple structure.

Figure 12A:
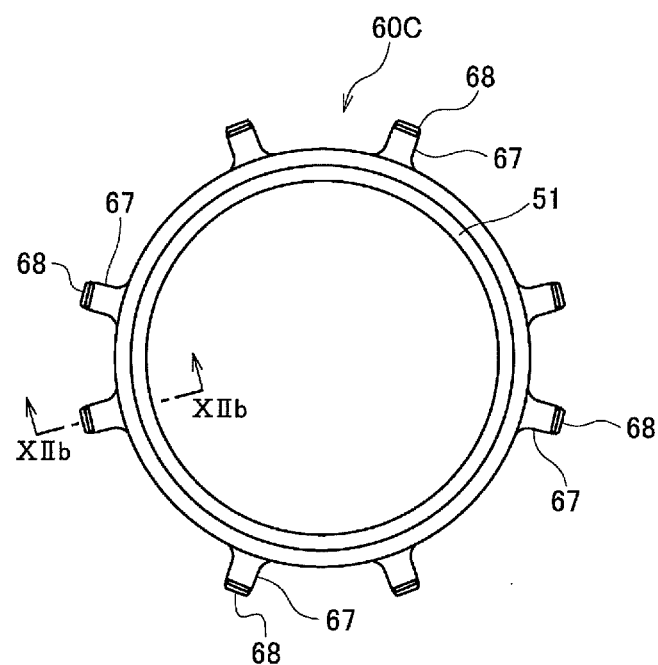
FIG. 12 is a block diagram of the lens holding ring according to further another embodiment of the present invention, wherein (a) is a plan view of the ring, and (b) is an expanded cross-sectional view taken along the line XIIb-XIIb of (a).
Figure 12B:
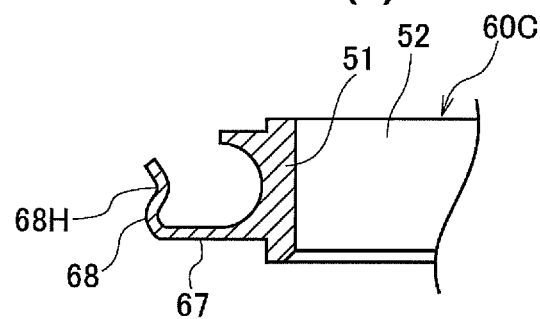

FIG. 12 is a block diagram of the lens holding ring according to further another embodiment of the present invention, wherein (a) is a plan view of this ring, and (b) is an expanded sectional view taken along the line XIIb-XIIb of (a).

In the lens holding ring 60C of this embodiment, all protruding pieces 57 and folded parts 58 in the lens holding ring 60 of FIG. 9 and FIG. 10 are arranged in the shapes of the protruding pieces 67 and the rising pieces 68 that constitute the projection part, thus making the shapes of all protruding parts uniform to one kind, and the design and manufacture can be facilitated.

Figure 13:
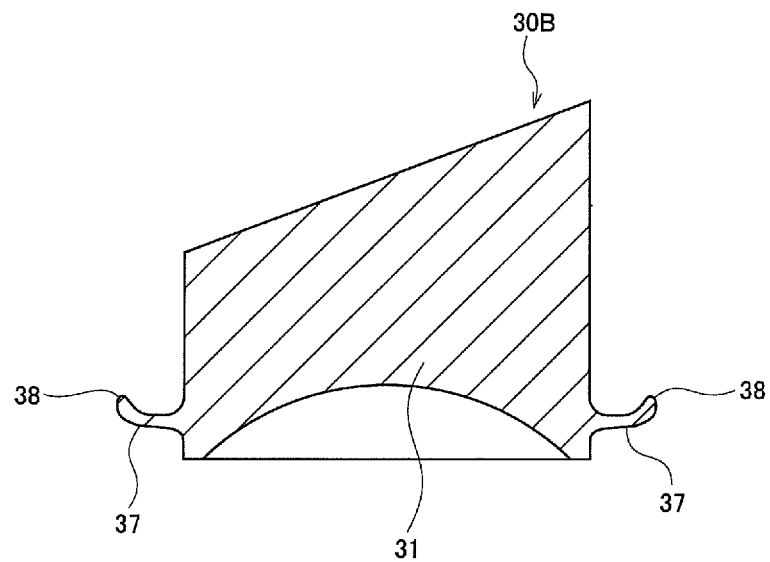
FIG. 13 is a cross-sectional view of the contact lens for vitreous surgery with engagement parts according to an embodiment of the present invention.
Figure 14:
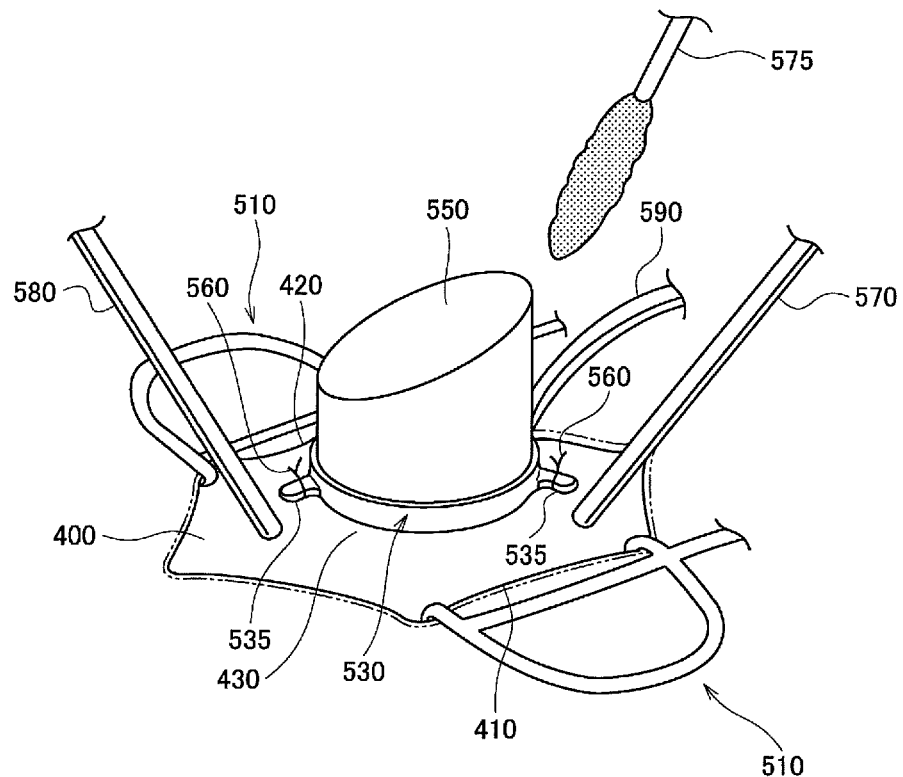
FIG. 14 is a perspective view showing a state that the lens holding ring is sutured to the sclera to perform vitreous surgery.
Figure 15A:
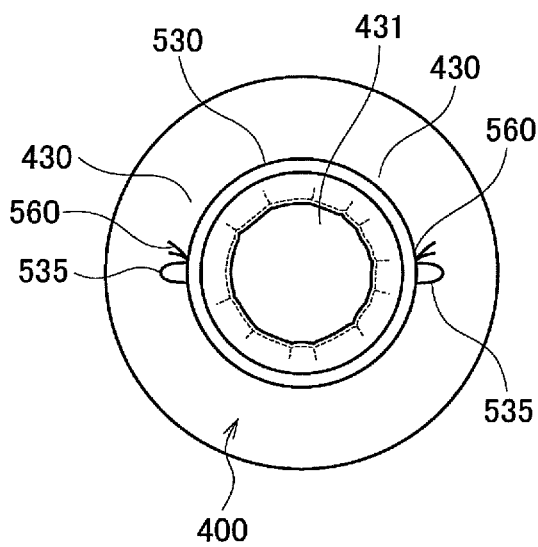
FIGS. 15(a) and 15(b) are plan views showing a state that a conventional lens holding ring is installed on an eyeball of a patient by suture.
Figure 15B:
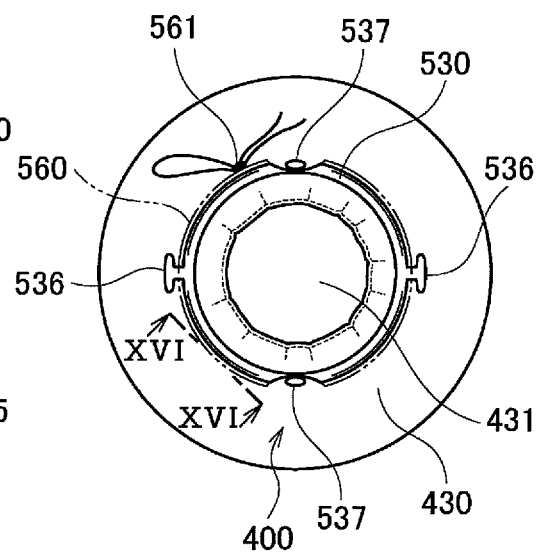
Figure 16:
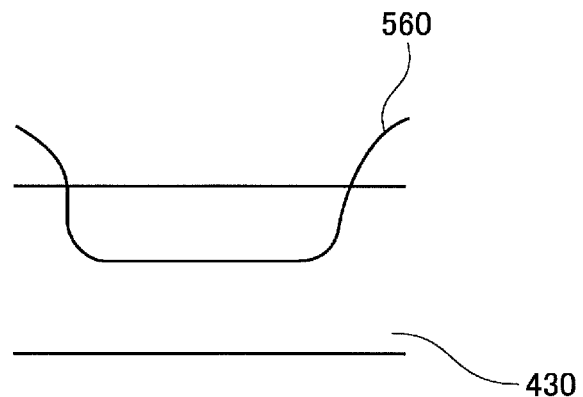
FIG. 16 is a cross-sectional view taken along the line XVI-XVI of FIG. 15(b).
Figure 17:
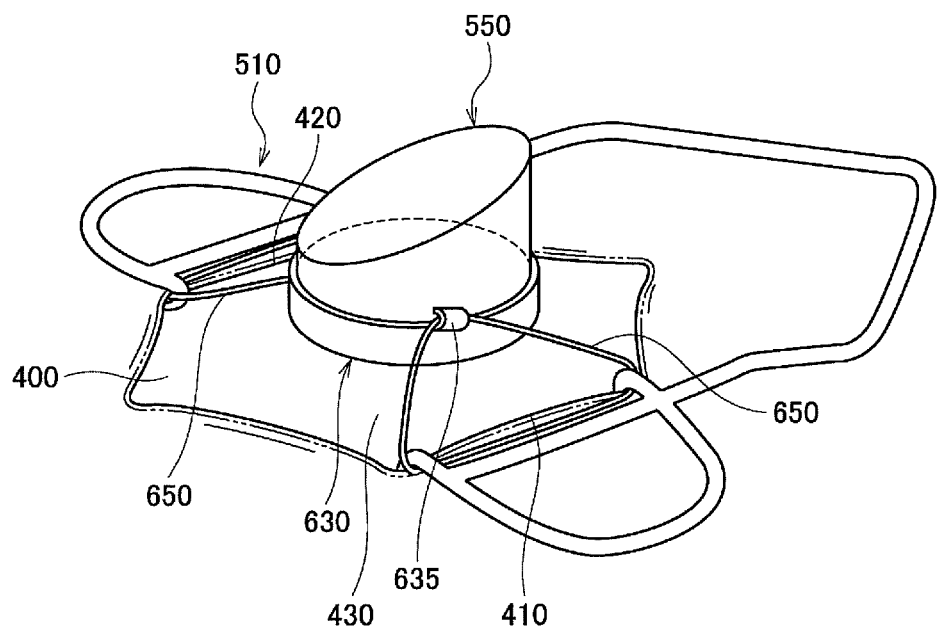
FIG. 17 is a perspective view showing a state that the lens holding ring is held on the eyeball by supporting it by an eyelid opener, and the contact lens for vitreous surgery is supported by this ring.
Figure 18:
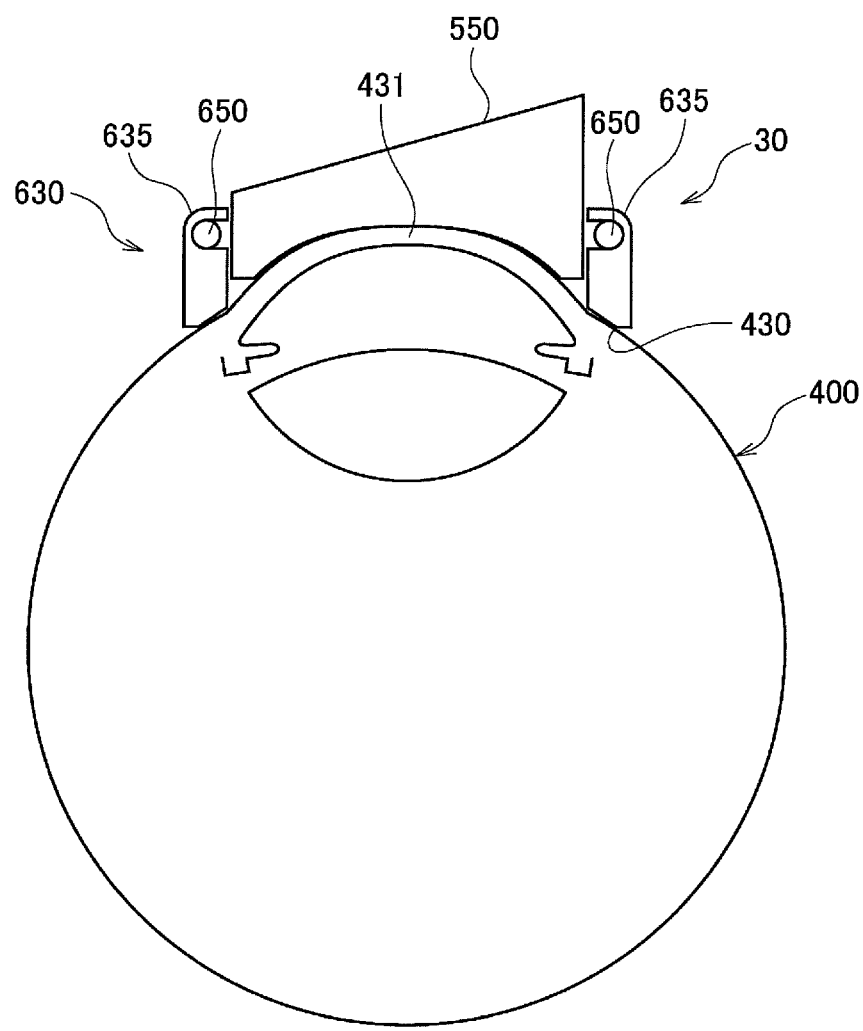
FIG. 18 is a cross-sectional view of the state of FIG. 17.

The above-described embodiments show a case that the surgery lens 30 is held using lens holding rings 50,50B, 50C, 50D, 50, 60B, and 60C. However, as shown in the example of FIG. 13, protruding pieces 37, being the engagement parts, are directly provided on the outer circumferential part of the lens body 31 of the surgery lens 30B, so that the string-like body 40a can be hooked on protruding pieces 37. At this time, similarly to the lens holding ring 50, folded parts 38 are preferably provided on the tips of the protruding pieces 37.

Thus, when the engagement parts (protruding pieces 37) for hooking the rubber band 40, are provided directly on the outer circumferential part of the lens body 31 of the contact lens 30B for vitreous surgery, the angle range for providing the engagement parts (protruding pieces 37) is preferably limited similarly to the example of FIG. 4. The same thing can be said for the number of the engagement parts (protruding pieces 37) and an interval between them. Further, a ring-shaped groove into which the string-like body (rubber band 40) is inserted, may be formed on the outer circumferential surface of the lens body 31, and the protruding piece 37 may be protrusively formed on the tip of the lower side wall of the groove, being the eyeball side in use. Further, similarly to the example of FIG. 6, the engagement parts (protruding pieces 37) may be provided as ring-shaped protrusions continuous in the circumferential direction of the lens body, or similarly to examples of FIG. 7 and FIG. 8, a continuous ring-shaped groove is formed in the circumferential direction on the outer circumference of the lens body, and the lower side wall, being the eyeball side, of both side walls of the ring-shaped groove may be utilized as the ring-shaped protrusions.

Further, when the string-like body (rubber band 40) is directly hooked on the contact lens 30B for vitreous surgery, substantially similar effect as a case using the lens holding rings 50, 50B, 50C, and 50D, can be obtained, and also the number of appliances necessary for the surgery can be reduced because the lens holding ring is eliminated.

Note that the temporary holding part of the string-like body which functions similarly to the temporary holding part of the string-like body shown in FIG. 9 to FIG. 12, can be provided in the lens body 31.

In this case, when the rubber band is installed on the outer circumferential part of the lens body 31, the parts opposed to each other across the opening of the ring in the rubber band, can be temporarily held by the temporary holding part of the string-like body. In addition, in this state, a prescribed space similar to the space shown in FIG. 9(*b*) can be secured between the rubber band and the outer circumference of the lens body 31, and between the rubber band and the lower surface of the lens body 31 respectively.

Specifically, for example, mutually separated projection parts, two as a set, are provided as the temporary holding parts of the string-like body, at opposed positions, with the lens body 31 on the outer circumferential part of the lens body interposed between them, thus forming a depression on the outside surface of each projection part, for hooking the rubber band thereon. Wherein, as shown in FIG. 9 and FIG. 10, the shape of the projection part may be formed in a shape of a bent strip plate, or as shown in FIG. 11, it may be formed in a block-shape. Further, the shape of the protruding piece 37 and the folded part 38 may be arranged in the shape of the projection part.

Further, when the string-like body formed in the ring shape by the elastic member, is installed on the outer circumference of the lens body 31, the temporary holding part of the string-like body composed of two projection parts as a set may be disposed at the positions opposed to each other in a direction approximately orthogonal to a line connecting protruding pieces formed at the positions opposed to each other.

By providing such a temporary holding part of the string-like body in the lens body 31, similar effect as the case of the lens holding ring shown in FIG. 9 to FIG. 12 can be exhibited.

DESCRIPTION OF SIGNS AND NUMERALS

1 Eyeball
2 Sclera
21, 22 Cannula (support member)
30, 30B Surgery lens (contact lens for vitreous surgery)
37 Folded part
40 Rubber band (string-like body)
40*a* String-like body
50, 50B, 50C, 50C Lens holding ring (holding device)
51 Lens body (lens holder)
52 Opening
53 Groove
53D Ring-shaped groove
57, 57C, 57D Protruding piece
58, 58D Folded part
60, 60B, 60C Lens holding ring (holding device)
62 String-like body temporary holding part
67B Projection part
68 Rising piece
68H Depression
S1, S2 Space

The invention claimed is:

1. A contact lens holding device for holding a vitreous surgery contact lens on an eyeball with a sclera during vitreous surgery, the contact lens holding device comprising:
  a lens holder having an inner surface defining an opening configured to receive the vitreous surgery contact lens, an outer surface, a groove that defines an upper end and a lower end and extends inwardly from the outer surface towards the inner surface, and a lower side wall at the lower end of the groove;
  engagement parts extending radially outwardly from the lower side wall of the lens holder at positions opposed to each other;
  first and second support members, each support member including a longitudinal axis, a first portion configured to be inserted into and fixed to the sclera, and a second portion that is larger than the first portion in a direction perpendicular to the longitudinal axis; and
  a string-like body sized and shaped to extend in tension along the surface of the eyeball around the first support member, over the engagement parts, and around the second support member when the first and second support members are fixed to the sclera on opposite sides of the lens holder.

2. The contact lens holding device for holding a vitreous surgery contact lens according to claim 1, wherein the location of the engaging parts results in the string-like body pressing the lens holder against the surface of the eyeball.

3. The contact lens holding device for holding a vitreous surgery contact lens according to claim 2, wherein
  the string-like body contacts the groove over angle ranges on opposite sides of the lens holder; and
  the engagement parts are respectively located within one of the angle ranges.

4. The contact lens holding device for holding a vitreous surgery contact lens according to claim 3, wherein a plurality of engagement parts are located within the angle ranges on both sides of the lens holder.

5. The contact lens holding device for holding a vitreous surgery contact lens according to claim 2, wherein the engagement parts comprise ring-shaped engagement parts.

6. The contact lens holding device for holding a vitreous surgery contact lens according to claim 2, wherein the engagement parts each include a tip end and a folded part at the tip end.

7. The contact lens holding device for holding a vitreous surgery contact lens according to claim 2, further comprising:
  temporary holding parts extending radially outwardly from the lens holder at positions opposed to each other across the opening.

8. The contact lens holding device for holding a vitreous surgery contact lens according to claim 7, wherein
  the engagement parts comprise first and second sets of engagement parts extending radially outwardly from the lower side wall of the lens holder at positions opposed to each other; and
  the temporary holding parts include depressions.

9. The contact lens holding device for holding a vitreous surgery contact lens according to claim 7, wherein
  the string-like body contacts the groove over angle ranges on opposite sides of the lens holder;
  the engagement parts are respectively located within one of the angle ranges; and
  the temporary holding parts are opposed to each other in a direction approximately orthogonal to a line connecting the engagement parts.

10. The contact lens holding device for holding a vitreous surgery contact lens according to claim 7, wherein the temporary holding parts each include a protrusive piece defining a tip, a rising piece extending upwardly from the tip and a depression on an outside surface of the rising piece.

11. The contact lens holding device for holding a vitreous surgery contact lens according to claim 10, wherein the engagement parts each include a protrusive piece defining a tip, a rising piece extending upwardly from the tip and a depression on an outside surface of the rising piece.

12. The contact lens holding device for holding a vitreous surgery contact lens according to claim 7, wherein the temporary holding parts extend radially outwardly from the lower side wall of the lens holder.

13. The contact lens holding device for holding a vitreous surgery contact lens according to claim 1, wherein the string-like body comprises a ring-shaped elastic member.

14. The contact lens holding device for holding a vitreous surgery contact lens according to claim 1, wherein the first and second support members comprise first and second cannulas.

15. A contact lens holding device for holding a vitreous surgery contact lens on an eyeball with a sclera during vitreous surgery, the contact lens holding device comprising:

a lens holder having an inner surface defining an opening configured to receive the vitreous surgery contact lens, and an outer surface that defines an upper end and a lower end; and at least two engagement parts mounted on the lower end of the outer surface of the lens holder at positions opposed to each other, the at least two engagement parts each including a first portion that extends radially outwardly from the lower end of the outer surface of the lens holder and defines a tip end, a second portion that extends upwardly from the tip end, and a depression located on an outside surface of the engagement part.

16. The contact lens holding device for holding a vitreous surgery contact lens according to claim 15, wherein the second portion is oriented at 45 degrees relative to the first portion.

17. The contact lens holding device for holding a vitreous surgery contact lens according to claim 15, wherein the at least two engagement parts comprise at least two sets of engagement parts.

18. The contact lens holding device for holding a vitreous surgery contact lens according to claim 15, further comprising:

temporary holding parts extending radially outwardly from the lens holder at positions opposed to each other across the opening.

* * * * *